(12) United States Patent
Ries

(10) Patent No.: US 11,547,424 B2
(45) Date of Patent: Jan. 10, 2023

(54) INSTRUMENT SET FOR SPINAL OPERATIONS

(71) Applicant: Joimax GmbH, Karlsruhe (DE)

(72) Inventor: Wolfgang Ries, Linkenheim (DE)

(73) Assignee: JOIMAX GMBH, Karlsruhe (DE)

( * ) Notice: Subject to any disclaimer, the term of this patent is extended or adjusted under 35 U.S.C. 154(b) by 0 days.

(21) Appl. No.: 16/982,933

(22) PCT Filed: Jan. 31, 2019

(86) PCT No.: PCT/EP2019/000030
§ 371 (c)(1),
(2) Date: Sep. 21, 2020

(87) PCT Pub. No.: WO2019/179653
PCT Pub. Date: Sep. 26, 2019

(65) Prior Publication Data
US 2021/0015501 A1     Jan. 21, 2021

(30) Foreign Application Priority Data

Mar. 21, 2018 (DE) ............ 10 2018 002 356.8
Aug. 14, 2018 (DE) ............ 10 2018 006 442.6

(51) Int. Cl.
*A61B 17/02* (2006.01)
*A61B 17/17* (2006.01)
(Continued)

(52) U.S. Cl.
CPC ...... *A61B 17/1757* (2013.01); *A61B 17/1671* (2013.01); *A61B 17/3421* (2013.01); *A61B 2017/564* (2013.01)

(58) Field of Classification Search
CPC . A61B 17/16; A61B 17/1602; A61B 17/1604; A61B 17/1659; A61B 17/1671;
(Continued)

(56) References Cited

U.S. PATENT DOCUMENTS 9,028,522 B1 * 5/2015 Prado ............... A61B 17/3417
606/191
2002/0156481 A1 * 10/2002 Boyd ................ A61B 17/1757
606/90
(Continued)

FOREIGN PATENT DOCUMENTS

DE         4328690 A1     3/1995
DE     202005016762 U1    11/2006
(Continued)

*Primary Examiner* — Eduardo C Robert
*Assistant Examiner* — Michelle C Eckman
(74) *Attorney, Agent, or Firm* — McGlew and Tuttle, P.C.

(57) ABSTRACT

A complete removal and reinsertion of instruments is avoided when the instruments are initially not correctly positioned during a minimally invasive operation on a bone, in particular a vertebra of the spine. This aim is achieved by an instrument set for spinal operations, including a guide rod, which has a cavity extending along the axis of the guide rod, and a guide tube, which can be received in the cavity of the guide rod, wherein the guide rod has a distal lip, which is arranged eccentrically to the cavity and/or to a center axis of the guide rod.

28 Claims, 21 Drawing Sheets

(51) Int. Cl.
*A61B 17/16* (2006.01)
*A61B 17/34* (2006.01)
*A61B 17/56* (2006.01)

(58) Field of Classification Search
CPC ... A61B 17/1703; A61B 17/02; A61B 17/025; A61B 2017/0256–0262
See application file for complete search history.

(56) References Cited

U.S. PATENT DOCUMENTS

| | | | | |
|---|---|---|---|---|
| 2003/0073998 | A1* | 4/2003 | Pagliuca | A61B 17/0293 606/264 |
| 2007/0066977 | A1 | 3/2007 | Assell et al. | |
| 2007/0288026 | A1* | 12/2007 | Shluzas | A61B 17/7083 606/86 A |
| 2015/0359570 | A1* | 12/2015 | Ries | A61B 17/3421 604/513 |
| 2016/0045334 | A1* | 2/2016 | Ries | A61F 2/447 623/17.16 |
| 2017/0021147 | A1* | 1/2017 | Predick | A61B 17/0206 |
| 2017/0135704 | A1* | 5/2017 | Abbasi | A61B 17/1637 |
| 2018/0256364 | A1* | 9/2018 | Sandhu | A61B 17/3421 |

FOREIGN PATENT DOCUMENTS

| | | |
|---|---|---|
| DE | 202005016763 U1 | 11/2006 |
| DE | 60032052 T2 | 7/2007 |
| EP | 1048271 A2 | 11/2000 |
| WO | 2014146797 A1 | 9/2014 |
| WO | 2015002204 A1 | 1/2015 |
| WO | 2017119401 A1 | 7/2017 |

* cited by examiner

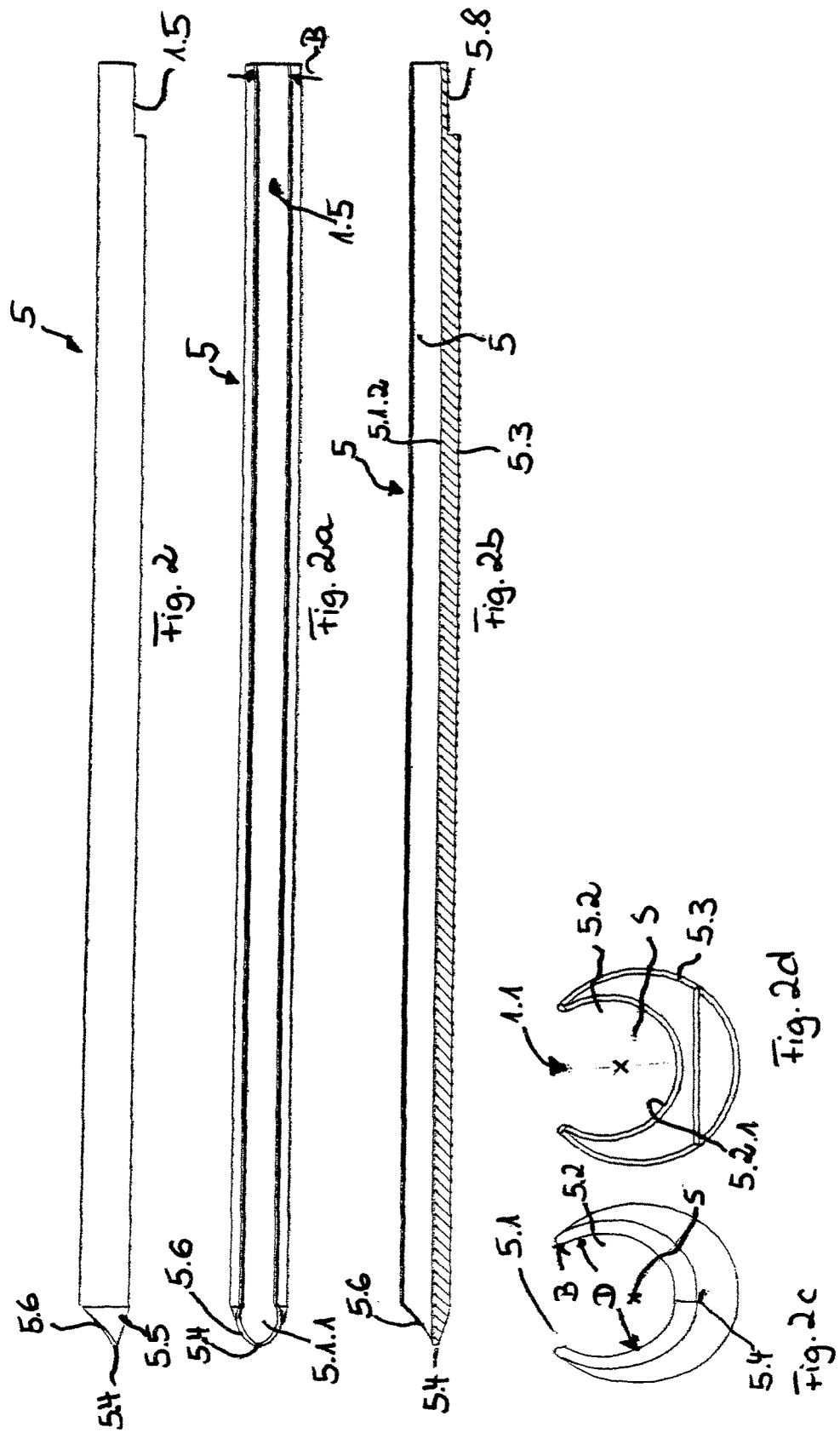

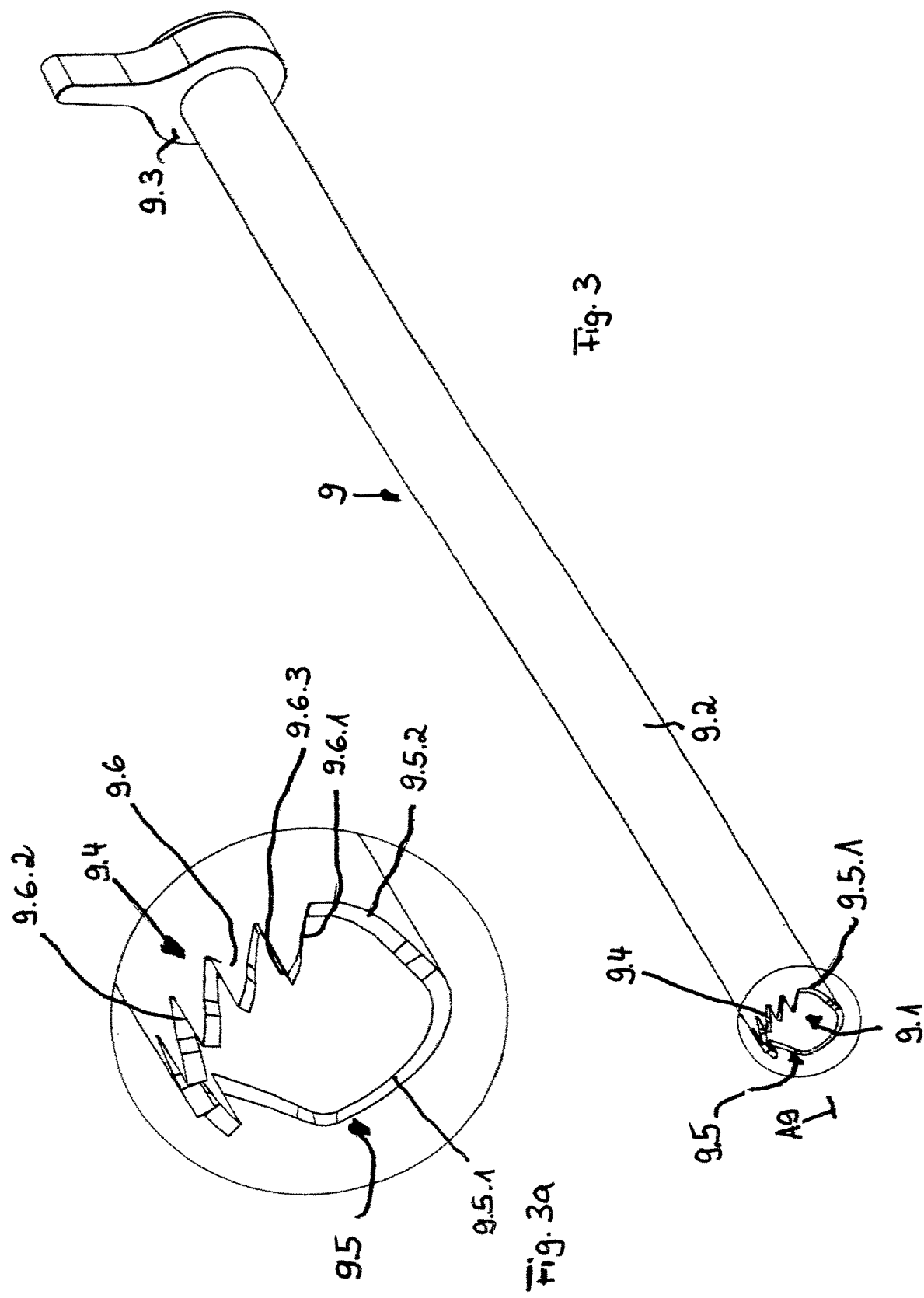

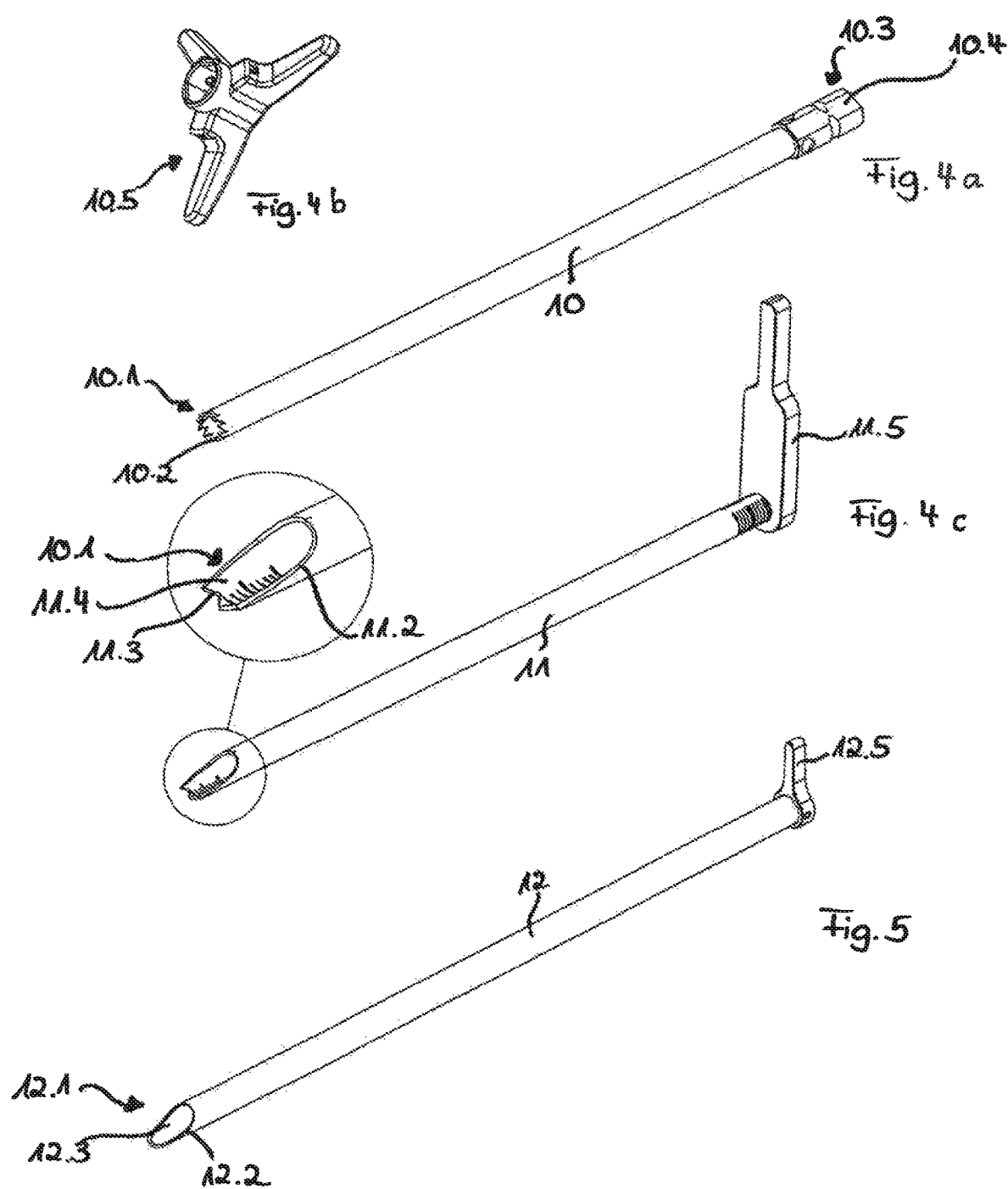

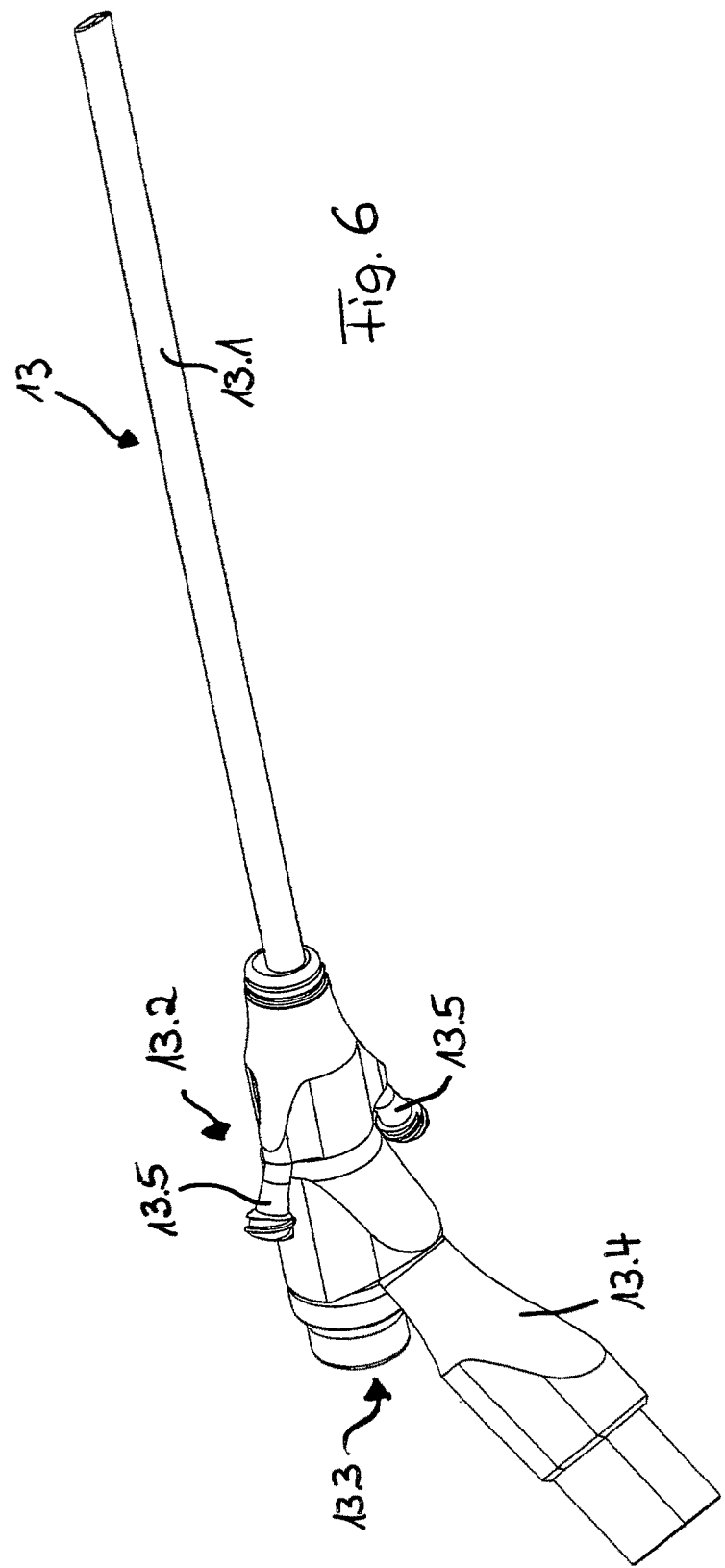

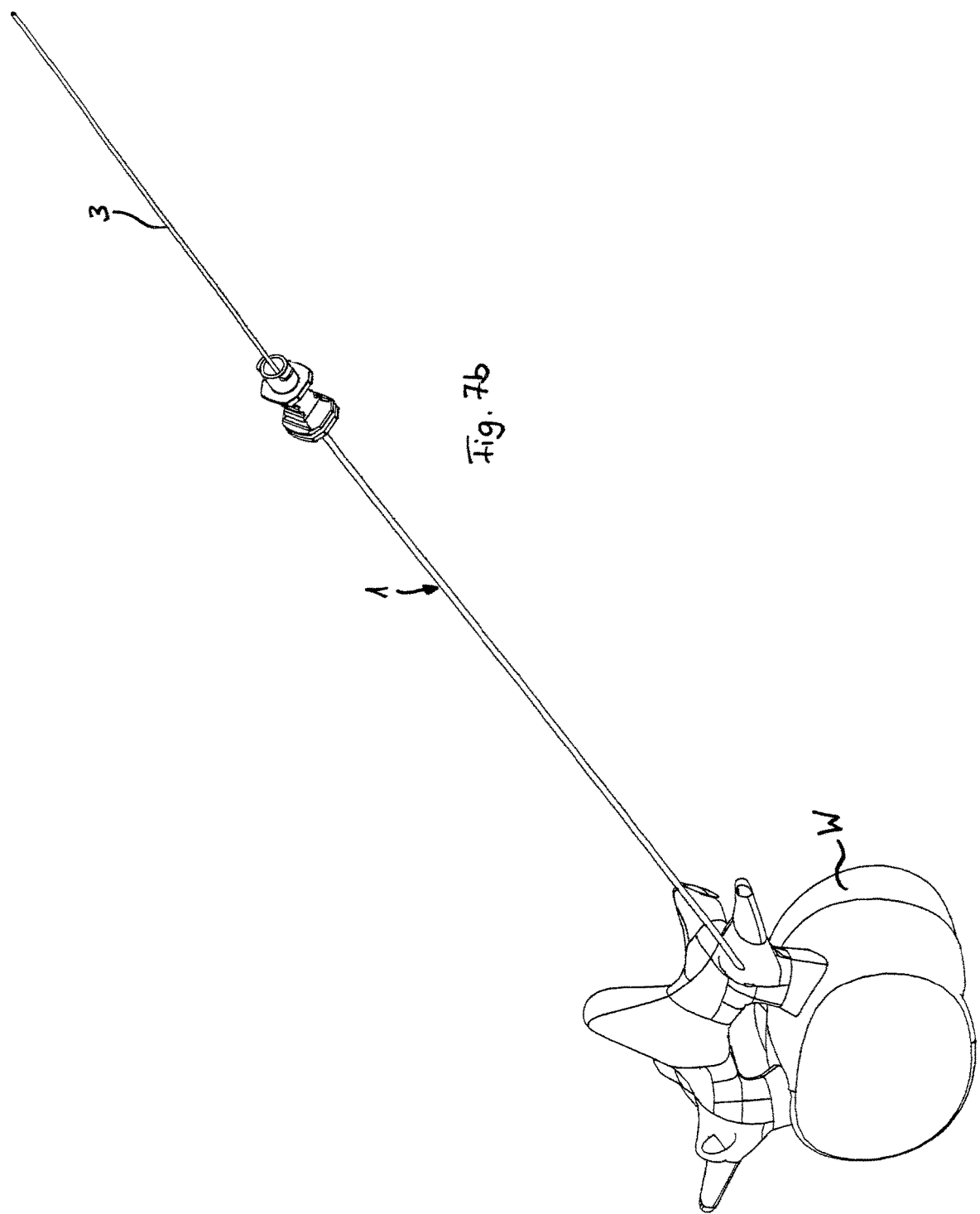

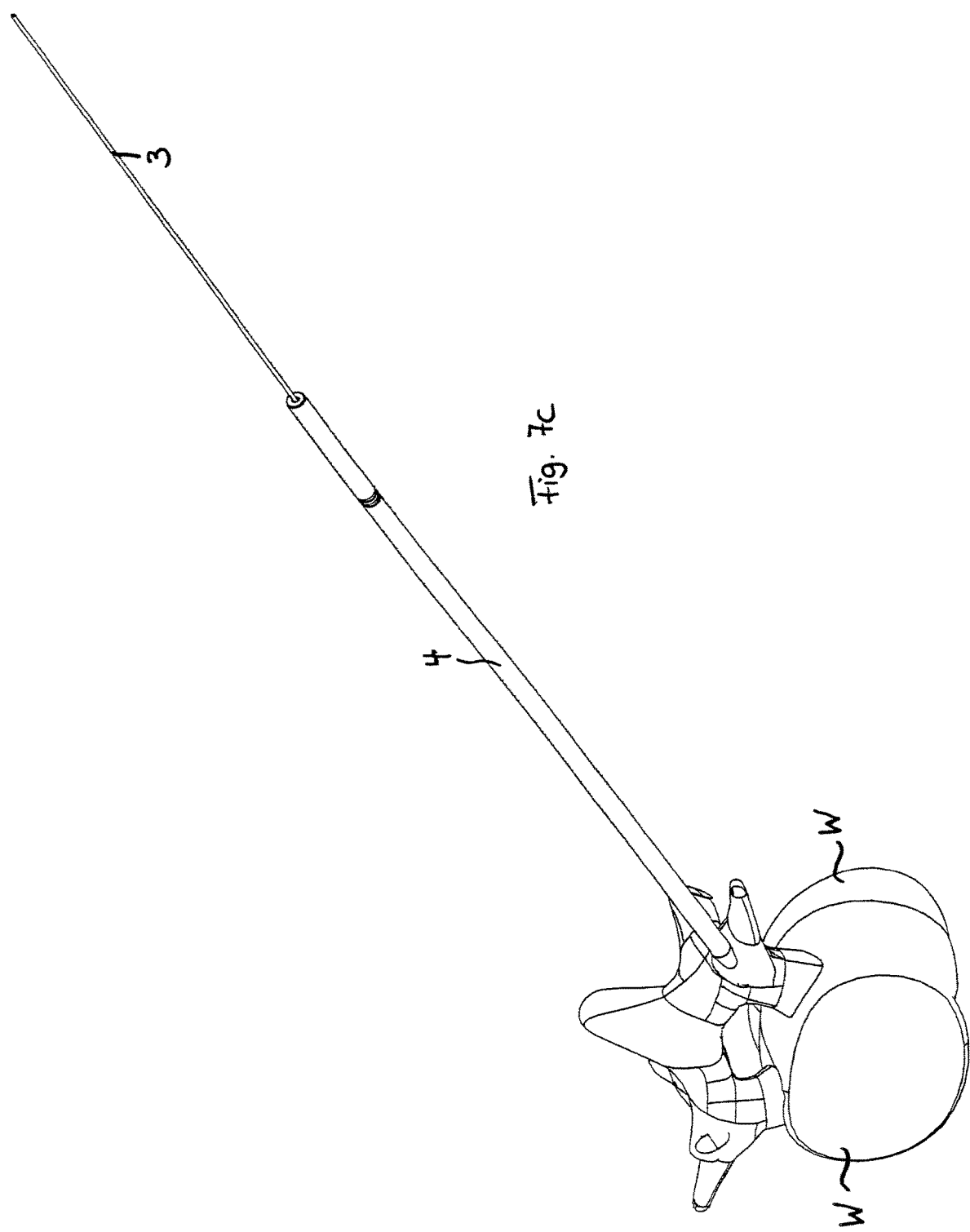

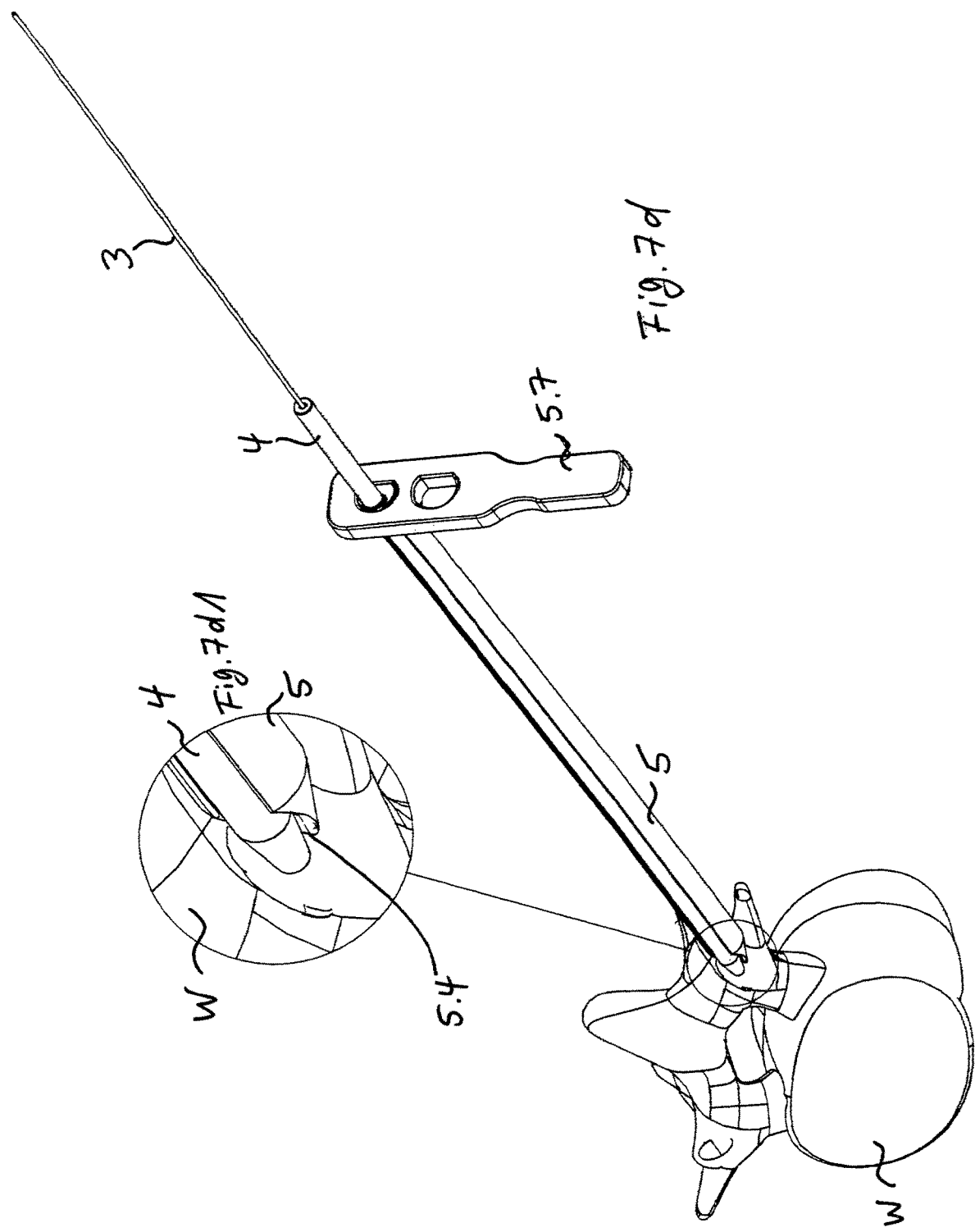

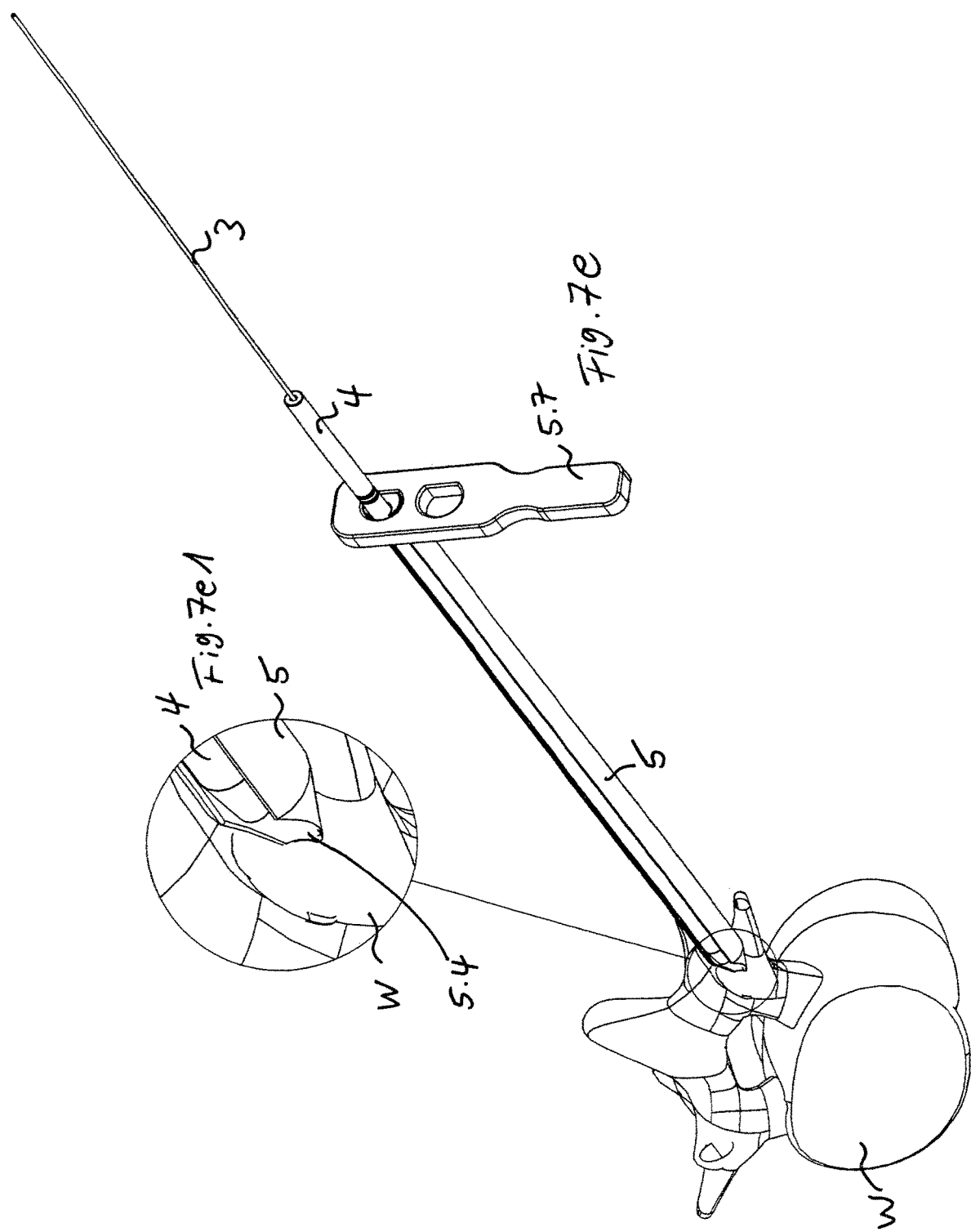

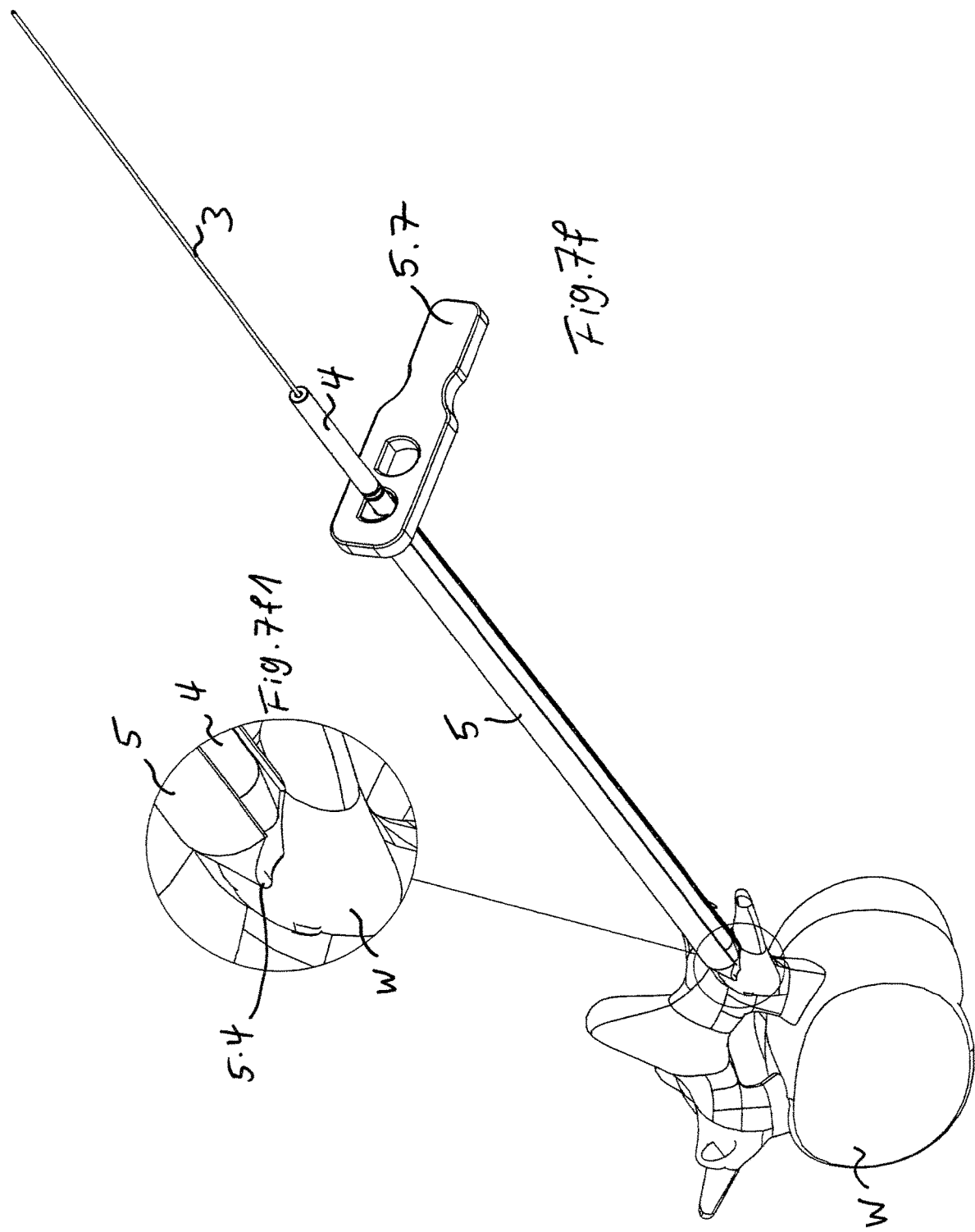

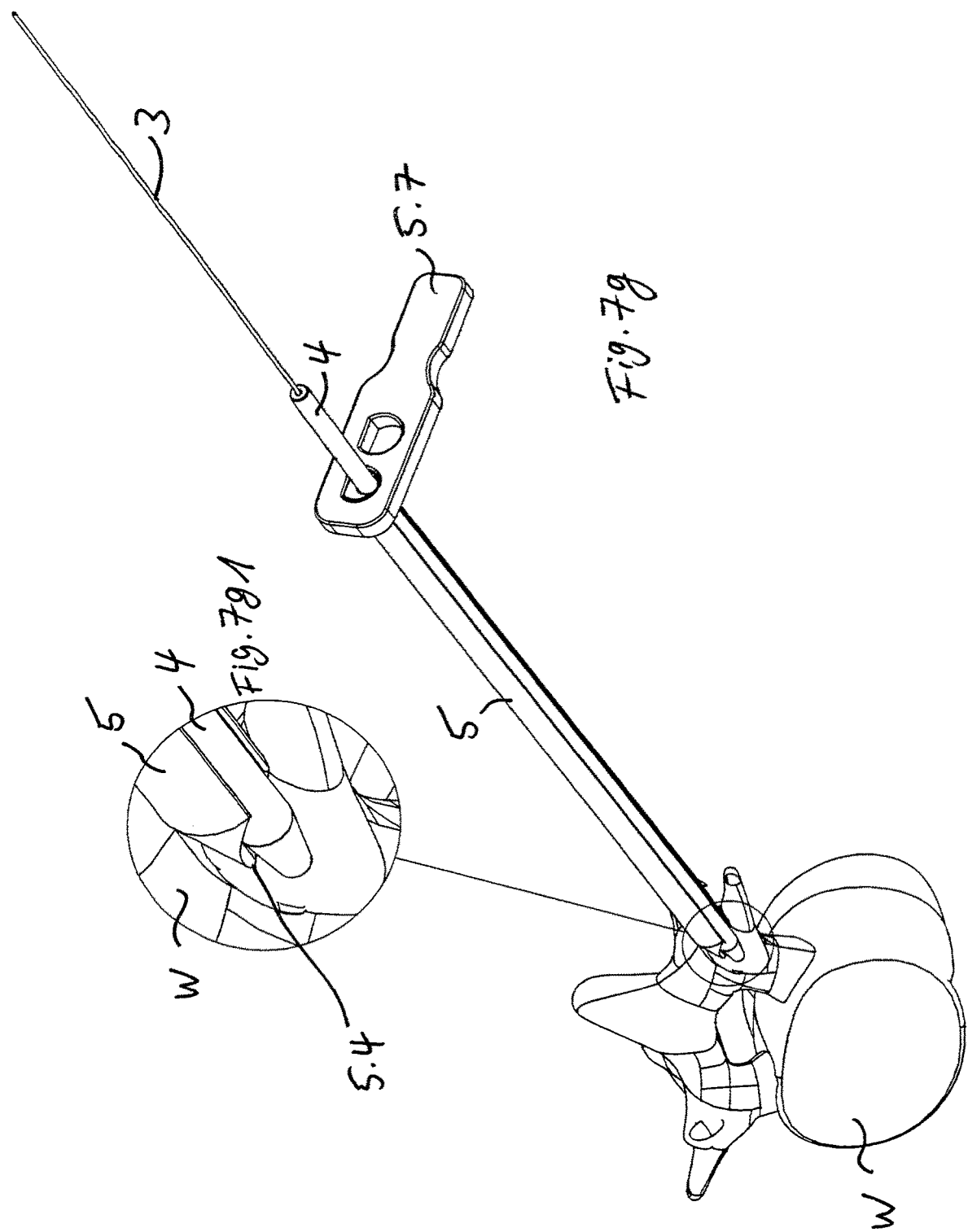

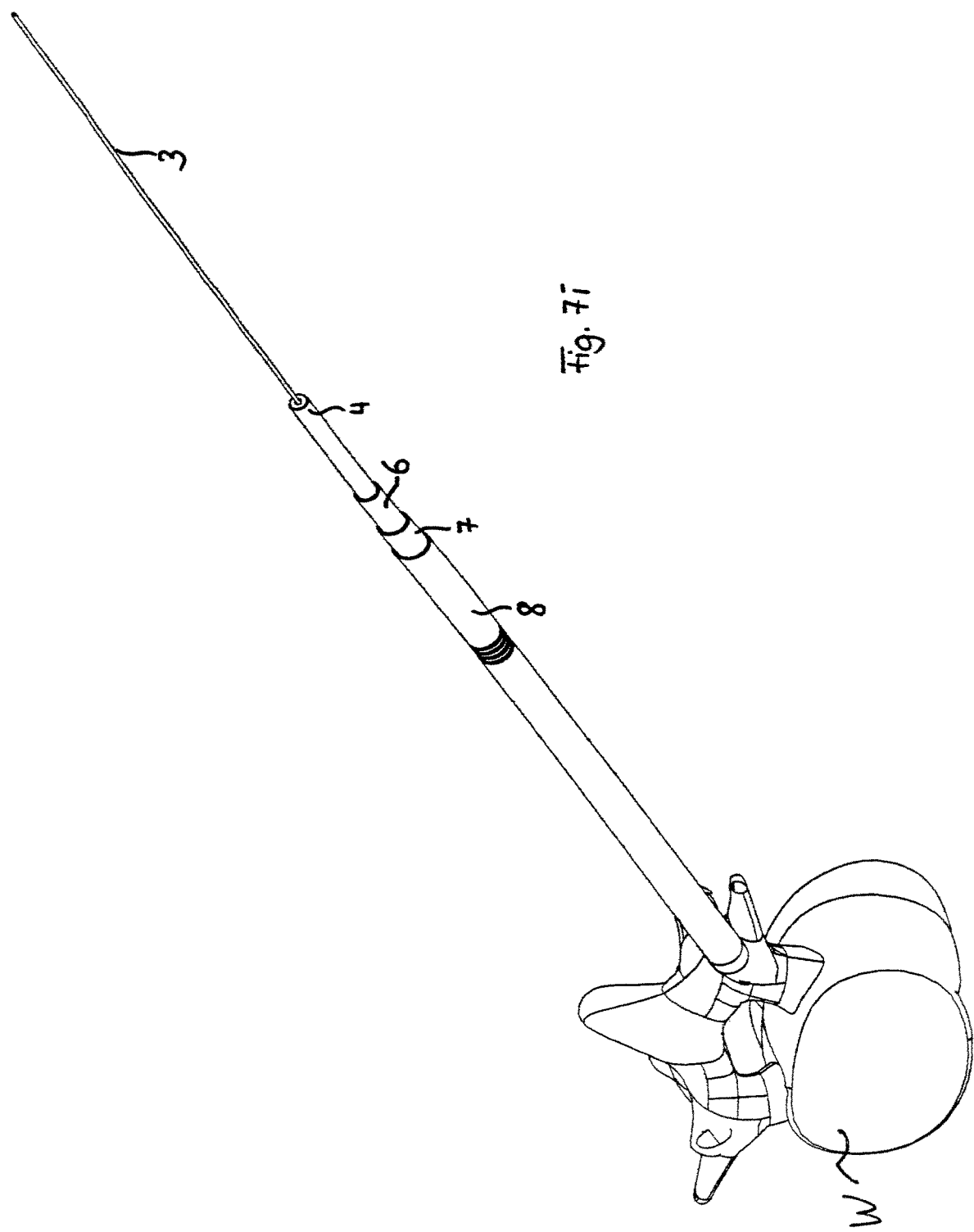

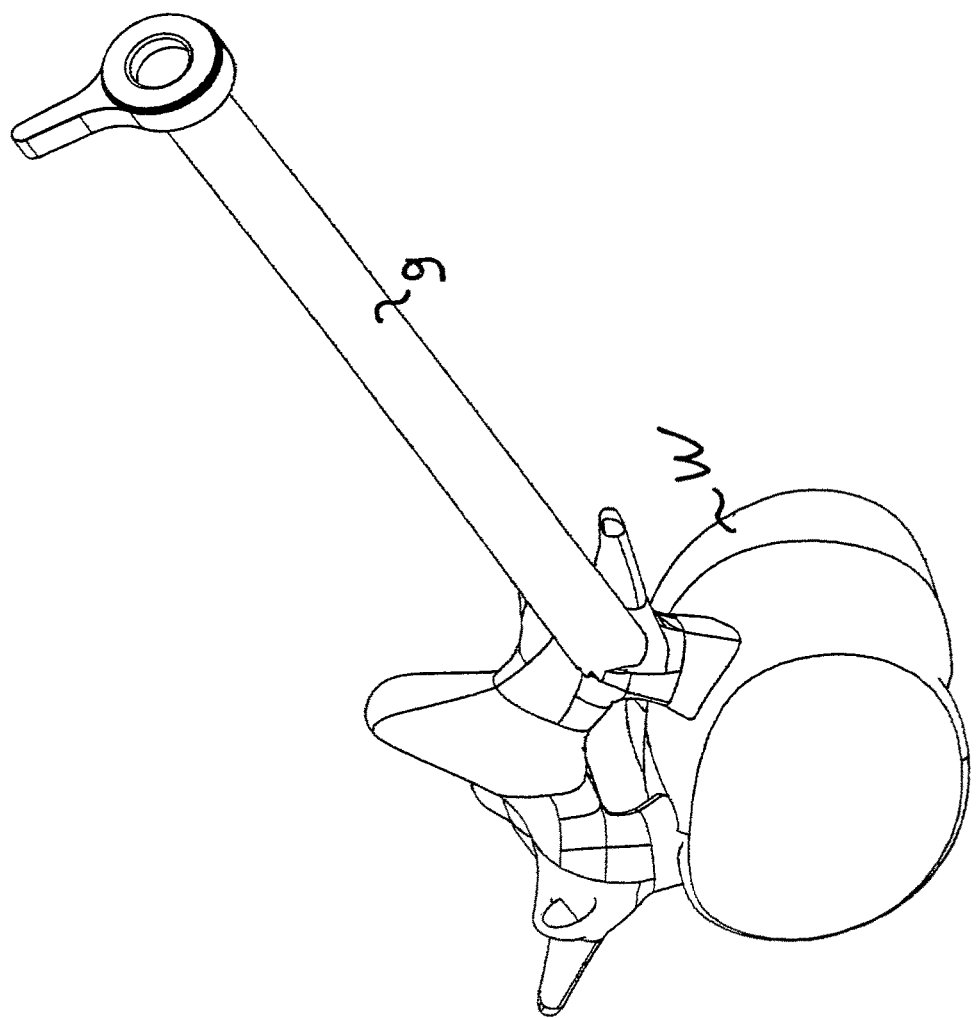

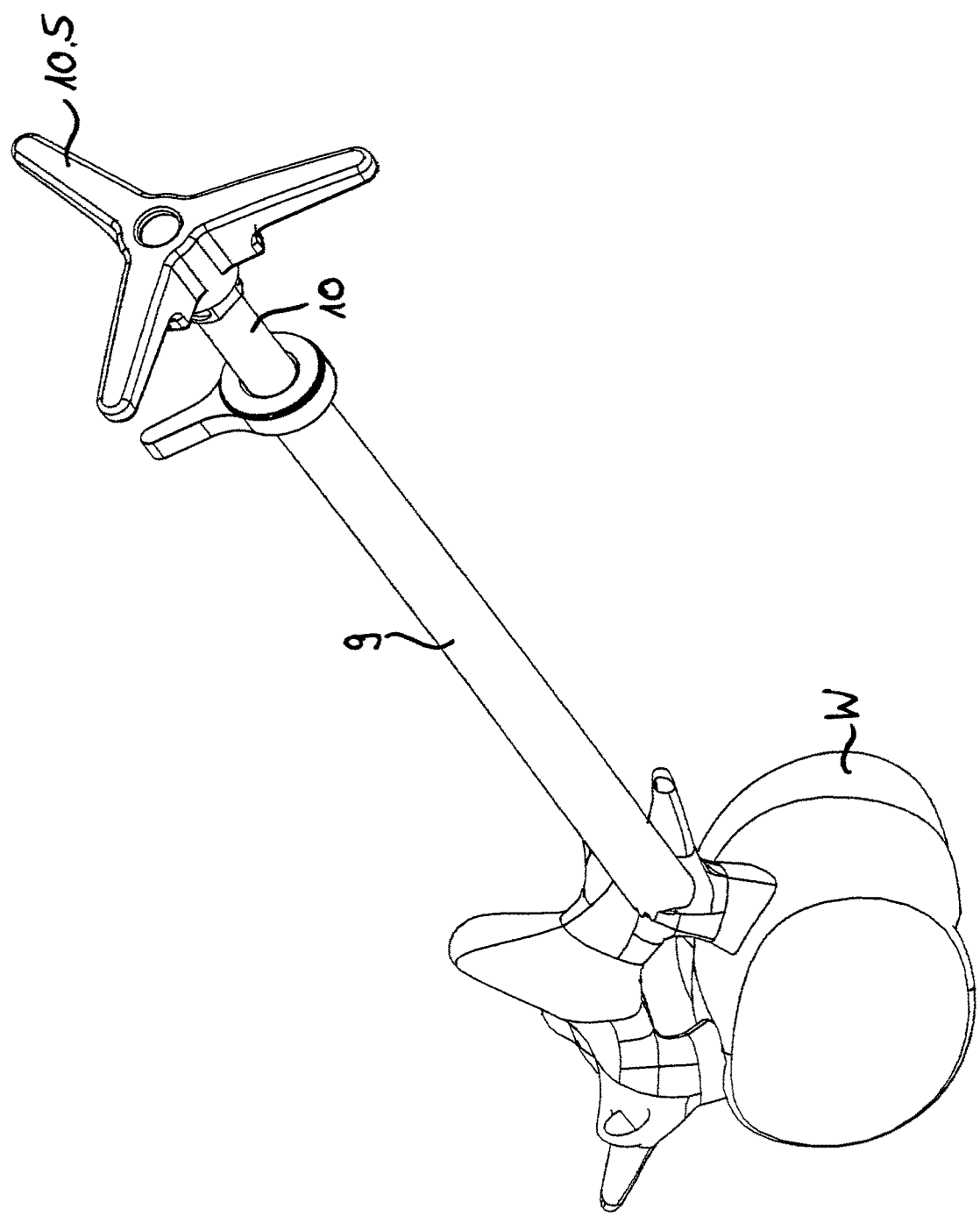
fig. 7ℓ

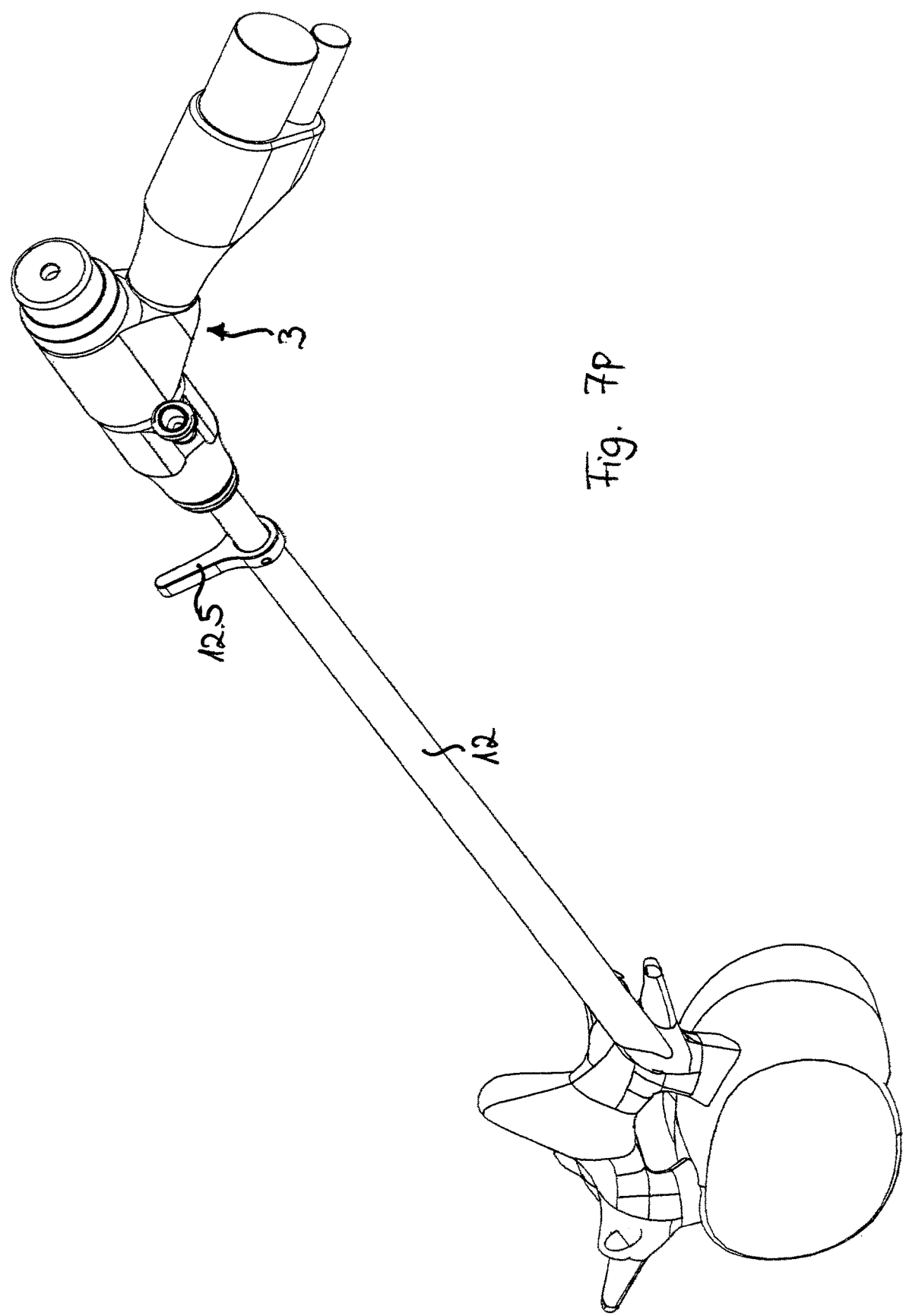

ly being
INSTRUMENT SET FOR SPINAL OPERATIONS

CROSS REFERENCE TO RELATED APPLICATIONS

This application is a United States National Phase Application of International Application PCT/EP2019/000030, filed Jan. 31, 2019, and claims the benefit of priority under 35 U.S.C. § 119 of German Application 10 2018 002 356.8, filed Mar. 21, 2018, the entire contents of which are incorporated herein by reference.

TECHNICAL FIELD

The invention relates to an instrument set for spinal operations, comprising a guide rod which has a cavity extending longitudinally with respect to the axis, and comprising a guide tube which can be received in the cavity of the guide rod.

TECHNICAL BACKGROUND

When inserting surgical instruments into a (human) body to an operating site, sometimes the surgeon does not find this site immediately, even under X-ray view, in particular if the operating region is narrow. It is then necessary to partially or completely withdraw the inserted instruments and to reinsert them to the correct operating site if possible, which is not only time-consuming but also stressful for the patient.

This applies, for example, to the removal of osteophytes, i.e. bone growths, in particular on vertebrae of the spine, which press on nerves and thus lead to considerable pain for a patient or which, if they occur on the front of vertebral projections (processes), can restrict mobility.

SUMMARY

An object of the invention is therefore that of providing an instrument set and proposing a method by means of which, within the scope of a surgical procedure, the operating site, i.e. the region where the distal ends of the instruments of an instrument set are located, can be corrected without having to pull the instruments out of the body.

In a further development, the cavity is eccentric with respect to the outer contour and/or the central axis of the outer contour of the guide rod. Furthermore, in a preferred embodiment of the invention, the guide rod has a distal tongue which is arranged eccentrically with respect to the cavity and/or a central axis of the guide rod.

In order to solve the aforementioned problem, the invention also relates to a method which is characterized in that, after a guide tube has been inserted from the body surface of a patient as far as the surface of a vertebral body or bone, a guide rod comprising an eccentrically formed cavity is inserted over the guide tube into the body of the patient as far as the surface of the vertebral body or bone, in that the position of the distal end of the guide cannula relative to an intended position is checked, generally under X-ray view, in that, if the intended operating region does not match the position of the distal end of the guide tube on the vertebral body or bone, a distal tip formed eccentrically at the distal end of the guide rod is pressed against the surface of the vertebral body or bone, in that the guide tube within the guide rod is retracted in a proximal direction, in that the guide rod together with the guide tube located therein is pivoted about its distal tip in order to pivot a cavity of the guide rod over the intended operating region or to move closer to the operating region, and in that the guide tube within the guide rod is subsequently moved again distally toward the surface of the vertebral body or bone.

The method according to the invention can in principle be used both transforaminally and interlaminarly.

By means of the instrument set according to the invention comprising a guide rod designed as stated above, it is possible in principle to press the eccentric tip of the distal tongue of said guide rod firmly against the surface of a vertebra or bone and then to pivot said guide rod about the tip of the tongue, whereby the cavity of the guide rod and a guide tube seated therein are also pivoted. In so doing, the location of the lumen and the cannula can be pivoted from an inappropriate position to a specific operating site. If necessary, this process can be repeated multiple times.

The method includes the individual method steps which are to be carried out by a surgeon in order to carry out the corresponding operation.

In a preferred development of the instrument set according to the invention, the cavity is eccentrically formed in the guide rod.

Moreover, in a preferred embodiment of the set, the guide rod can have a lateral slot opening connected to the cavity, such that the cavity forms a partially cylindrical groove, the width of the slot opening in particular being smaller than the diameter of the groove. For a given slot opening, this latter feature in particular prevents an instrument, for example a guide tube, inserted axially into the cavity thus formed as a groove, from moving laterally out of the groove of the guide rod.

In further embodiments, the width of the slot opening can be smaller than the diameter of the groove.

In further embodiments, the inner wall surface of the guide rod that surrounds the cavity or the groove is in the shape of a cylinder jacket or partial cylinder jacket and/or the outer wall surface of the guide rod is in the shape of a cylinder jacket casing or partial cylinder jacket. This ensures the compatibility of the guide rod with other instruments which are inserted therein or into which said rod is inserted or which are inserted via said guide rod.

In a further preferred embodiment, the slot opening of the cavity or the groove of the guide rod is diagonally opposite the tongue.

An extremely preferred development of the instrument set according to the invention is characterized by a working sleeve comprising a longitudinally extending, in particular cylindrical cavity which has a cross section that is at least the same as the cross section of the guide tube, preferably as the cross section of the guide rod.

In a preferred embodiment, the working sleeve in this case has a row of teeth on its distal end face, which row of teeth extends over part of the circumference of the working sleeve, preferably over half the circumference.

The teeth of the row of teeth are in particular asymmetrical, a first flank of the teeth being designed as a flat S inclined towards the distal tip of a tooth while a second flank is oriented axially parallel.

Opposite the row of teeth, a tongue having a continuous distal end face extends preferably over part of the circumference of the working sleeve. In particular, the tips of the teeth and the end face of the tongue are at the same axial height.

The operation set can be further developed by a hollow needle comprising a stylet and/or a guide wire, transverse dimensions of the stylet and/or guide wire preferably being adapted to the lumen of the cavity of the hollow needle, and/or by dilators comprising lumina adapted to the guide tube and/or guide rod or to one another. Moreover, the operating set is further developed by work tools such as milling cutters and the chisel, the radial dimensions of which are adapted in particular to the lumen of the working sleeve.

In developments of the method according to the invention, a guide rod comprising a cavity arranged eccentrically in its outer contour and/or the axis of symmetry of its outer contour is inserted into the body of the patient and/or one or more dilators are firstly introduced over the guide tube or guide rod as far as the vertebral body and the working sleeve is subsequently inserted over the inserted dilator having the largest diameter and/or firstly, optionally after making a skin incision, a hollow needle having an inserted stylet is inserted into the body of the patient as far as the vertebral body, then the stylet is removed and a guide wire is inserted through the hollow needle, and then, after removing the hollow needle, the guide tube is inserted over the guide wire as far as the vertebral body and finally the further steps of the method are carried out.

The method according to the invention can in particular be further developed in that at least one work instrument is inserted through the working sleeve as far as the operating site on the vertebral body or bone, and the operation to be performed, such as the removal of osteophytes, is carried out on the vertebral or bone surface, or in that the shaft of an endoscope is inserted through an elongate cavity of the work instrument.

It is also preferable for an endoscope to be firstly inserted through the working sleeve and then for a work instrument to be inserted through an elongate cavity of the endoscope as far as the surface of the vertebral body or bone, and for an operation step, such as the removal of an osteophyte, to be carried out under endoscopic view.

In the event that the instrument or instrument set has not been inserted precisely onto an operating site, such as on a vertebral body or a bone, the invention altogether makes it possible to achieve precise repositioning by means of pivoting such that the exact operating site can be occupied accurately, under X-ray and/or endoscope view, by the distal ends of the instruments to be provided.

Further advantages and features of the invention can be found in the claims and in the following description, in which embodiments of the invention are explained in detail with reference to the drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a lateral view of a guide rod according to the invention;

FIG. 2a is a lateral view of the guide rod, which view is offset by an angle of 90° around the axis of the guide rod;

FIG. 2b is a longitudinal section through the guide rod of FIGS. 1a and 1b;

FIG. 2c is a view of the distal end of the guide rod;

FIG. 2d is a view of the proximal end of the guide rod;

FIG. 3 shows a working sleeve of the instrument set according to the invention;

FIG. 3a is an enlarged view of the distal end of the working sleeve;

FIG. 4a is a perspective view showing a milling cutter of a set of working instruments;

FIG. 4b a perspective view showing an attachable grip for the milling cutter of FIG. 4a;

FIG. 4c is a perspective view showing a chisel of the set of working instruments;

FIG. 5 shows a guide sleeve;

FIG. 6 shows an endoscopic part of an instrument set according to the invention;

FIG. 7b shows the further method step of inserting a guide wire into the hollow needle after the removal of the obturator;

FIG. 7c shows the step of inserting the guide tube over the guide wire;

FIG. 7d shows the insertion of the eccentric guide rod comprising a handgrip in a first angular position over the guide tube;

FIG. 7d1 is an enlarged view of the distal region of the parts of FIG. 7d;

FIG. 7e shows the retraction of the guide tube in the proximal direction within the eccentric guide rod while the angular position is maintained, such that the tip of the eccentric guide rod sits on the vertebra;

FIG. 7e1 is an enlarged view of the distal region of the parts of FIG. 7e;

FIG. 7f shows the eccentric guide rod together with the inserted guide tube in a position of the eccentric guide rod that is pivoted by 90° about the distal tip of the guide rod relative to the orientation of FIGS. 7d to 7e1;

FIG. 7f1 is an enlarged view of the distal region of FIG. 7f;

FIG. 7g shows the advancement of the guide tube until it can be seen on the vertebra and the retraction of the eccentric guide tube in the angular position of FIG. 7f;

FIG. 7g1 is an enlarged view of the distal region of the parts of FIG. 7g;

FIG. 7i is a view after the insertion of a third dilator;

FIG. 7k shows, after the removal of the other elements, only the working sleeve comprising the handgrip, which working sleeve rests on the vertebra;

FIG. 7l shows the insertion of a milling cutter comprising a wing grip into the working sleeve;

FIG. 7o shows the insertion of a guide sleeve into the working sleeve and subsequently removal of the latter; and FIG. 7p shows the insertion of an endoscope into the guide sleeve.

DESCRIPTION OF PREFERRED EMBODIMENTS

Figures 1, 1A:
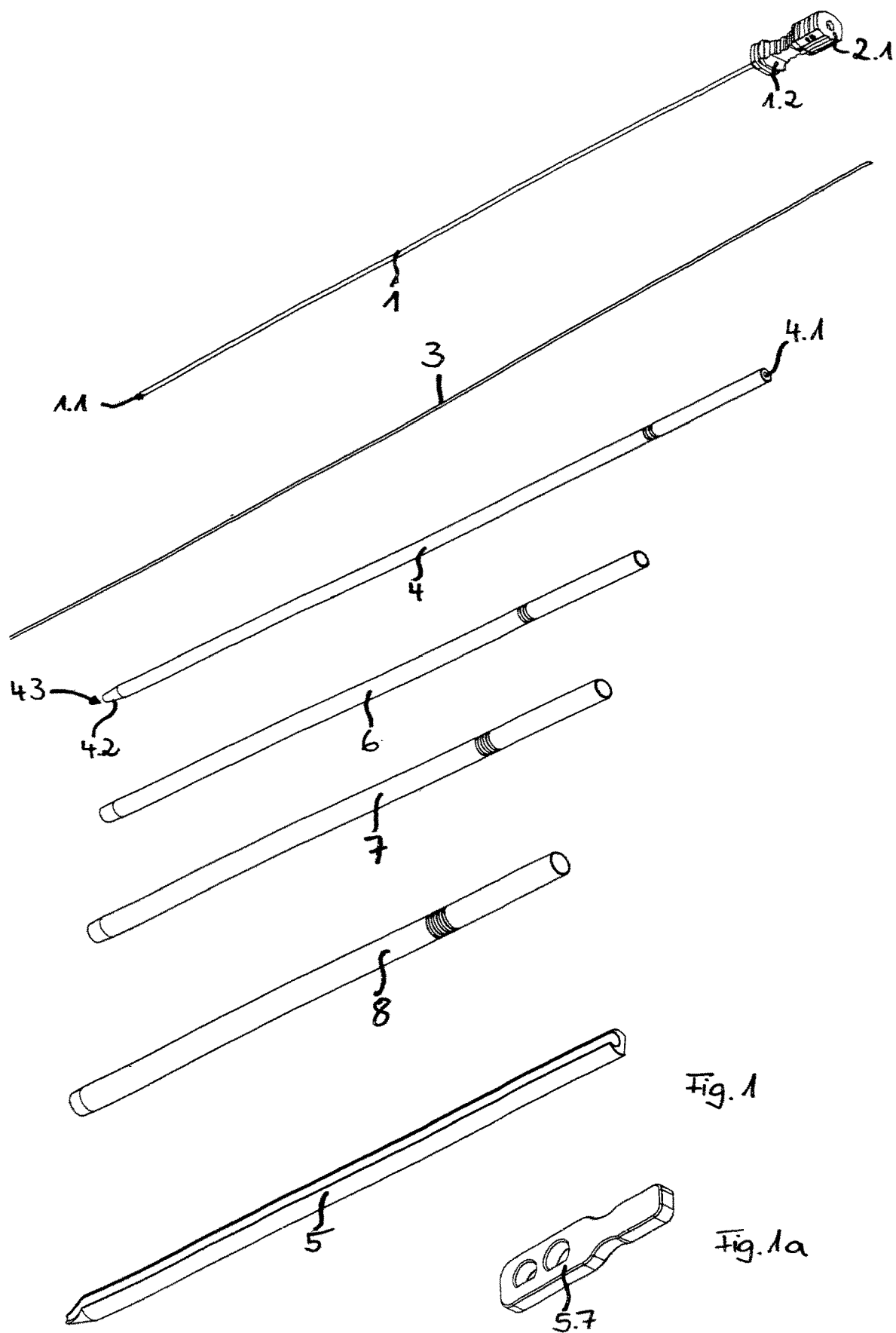
FIG. 1 shows a partial instrument set for inserting and positioning a working sleeve.
FIG. 1a shows an attachable grip of a guide rod of the partial instrument set of FIG. 1.

As shown in FIG. 1, an instrument set according to the invention substantially comprises the following parts:

A hollow needle 1 comprising a beveled distal end 1.1 and a grip part 1.2. A stylet (not shown) comprising a handgrip 2.1 is inserted into the hollow needle 1, the distal end face of which stylet is aligned with the beveled distal end 1.1 of the hollow needle. The instrument set also comprises a guide wire 3, the diameter of which is adapted to the lumen of the cylindrical cavity of the hollow needle 1. Another part of the set is a hollow cylindrical guide tube 4, the lumen of which is preferably also adapted to the diameter of the guide wire.

Another essential part of the instrument set is an eccentric guide rod 5, the lumen of which is adapted to the outer contour of the guide tube 4. The eccentric guide rod includes a grip 5.7 (FIG. 1*a*) that can be non-rotatably attached to the proximal end of said guide rod. Further parts include a first dilator 6, a second and a third dilator 7, 8, the cavities of the first dilator 6 likewise being adapted to the outer contour of the guide rod and the cavities of the second dilator 7 and the third dilator 8 being adapted to the outer contour of the first dilator 6 or the second dilator 7, respectively.

The above mentioned parts 4 to 7 are conically tapered on the outside at their distal end, so as to produce a continuous transition from an inner part to an outer part.

FIGS. 2*a* to 2*d* show an eccentric guide rod 5 according to the invention comprising a partially cylindrical groove 5.2 provided with a lateral slot opening 5.1. The outer wall surface or outer contour 5.3 of the guide rod 5 is, with the exception of the slot opening 5.1, partially cylindrical over the majority of the length with an axis of symmetry S of the cylindrical outer contour of FIGS. 2*c* and 2*d*. The groove 5.2 is eccentric to the axis of symmetry S. At its distal end, the slot opening 5.1 merges into a distal opening region 5.1.1, such that the distal end of the guide rod 5 is formed by a distal tip 5.4 which is also eccentric to the axis of symmetry S. Both the outer wall surface 5.3 and the inner wall surface 5.2.1 of the guide rod 5 that surrounds the groove 5.2 are partially cylindrical, with the exception of the lateral slot opening 5.1.

Edges 5.6 in the distal end region of the guide rod 5 extend, in the lateral plan view of FIG. 2*a*, in a convex arcuate shape into the distal tip 5.4 of a distal tongue 5.5, with FIG. 2*b* showing a cross-sectional view of a slightly concave shape of the edges 5.6.

At the proximal end, the guide rod 5 has a lateral flattened portion 1.5 of the longitudinal wall, such that a grip 5.7 (for example FIG. 1*a*) can be connected to the proximal end of the guide rod 5 in a non-rotatable but detachable manner.

The embodiment of the eccentric guide rod 5 comprising both the groove 5.2, which is eccentric to the axis of symmetry S (FIGS. 2*c* and 2*d*), and the tip 5.4, which is oriented eccentrically to the axis of symmetry S, is used, by pivoting the guide rod 5 about the tip 5.4 which sits on the wall of a vertebral body 6 of the spine (in the following referred to as vertebra W for short), to displace the distal opening region of the groove 5.2, the position of which determines the point of impact of instruments on the outer wall of a vertebra W, in order to, if the initially inserted instruments of an instrument set of which the guide rod 5 is part are not inserted precisely, correct a precise positioning of the groove 5.2 and thus of the entry and exit point, determined thereby, of instruments on the outer wall of a vertebra, in order to for example thus be able to remove troublesome osteophytes from said vertebra using appropriate tools.

The guide tube 4 (FIG. 1) which has a cylindrical cavity 4.1 is substantially a guide tube such as is usually used as part of an instrument set or sets for spinal operations. The guide tube 4 is cylindrical over the majority of its length and has, as stated, a cylindrical cavity 4.1. The distal end region 4.2 extends slightly conically inward and can have a beveled end having a distal opening 4.3 also extending obliquely to its longitudinal axis.

FIG. 3 shows a working sleeve 9, the distal end of which is inserted over the guide rod 4 and optionally the eccentric guide rod 5, optionally with the previous use of dilators 6, 7, 8 inserted over the guide cannula, as far as the work/operating site, and through which, after the removal of the guide cannula and optionally the guide rod and dilators, work instruments are directly inserted or firstly an endoscope is inserted and then work instruments such as milling cutters, chisels, pliers or the like are inserted through a cylindrical cavity of the endoscope (for the work sequence see also FIG. 7).

The working sleeve 9 has a cylindrical jacket 9.2 surrounding a likewise cylindrical cavity 9.1. Said working sleeve is provided with a grip part 9.3 at its proximal end. The distal end has a row of teeth 9.4 extending over part of the circumference of the jacket 9.2, and a lip 9.5 opposite of said row of teeth.

The teeth 9.6 of the row of teeth 9.4 are asymmetrical. A first flank 9.6.1 extends substantially axially parallel to the central axis A9 of the working sleeve 9, while the opposing second flank 9.6.2 is designed as a flat S inclined relative to the extension of the axis A9. The distal end face 9.5.1 of the lip 9.5 is at the same axial height as the distal tips 9.6.3 of the teeth 9.6 and merges, on both sides, into the tooth base of the respective outer teeth 9.6 of the row of teeth 9.4 via curves 9.5.2.

The working sleeve 9 can be securely anchored to the bone material of a vertebra or bone by means of the teeth 9.6, while the distal lip 9.5 is used to protect sensitive body elements such as nerves, in particular against tools for working on the surface of the vertebra W or bone that are directly or indirectly inserted through the working sleeve 9.

FIG. 4 shows a work tool, referred to as a milling cutter 10, for removing bone material from bones, such as osteophytes. The milling cutter 10 has a distal end 10.1 comprising a front row on the end face that extends around the entire circumference, the teeth of which row are asymmetrical such that one flank of a tooth, namely the front flank, extends parallel to the axis of the milling cutter, while the other flank includes an angle therewith. The proximal end 10.3 of the milling cutter 9 is not circularly symmetrical, but is provided with one or more flattened portions 10.4 on the circumference, such that a star grip 10.5 (FIG. 4*a*) can be non-rotatably attached thereto, by means of which star grip the milling cutter 10 can be rotated in order to remove bone material by means of its distal row of teeth 10.2.

Another work tool is a chisel 11, as shown in FIG. 4*b*, which has a distal end 11.1 having a bevel 11.2. The distal end face 11.3 of the tongue 11.4 formed by the bevel 11.2 is also toothed or comprises a few teeth (in this case three teeth). This also allows bone material to be removed. For the (rotary) movement of the chisel 11, said chisel is non-rotatably provided with a grip 11.5 at its proximal end, which grip can also be removed non-destructively if necessary. The outer diameter of the parts 10, 11 is preferably adapted to the lumen of the working sleeve 9.

FIG. 5 shows a guide sleeve 12 which also has a bevel 12.2 at the distal end 12.1, by means of which bevel a lateral tongue 12.3 is formed which, in contrast to the chisel 11, is not designed as a tool. A grip 12.5 is also non-rotatably attached at the proximal end of the guide sleeve 12, which grip can also be removed non-destructively if necessary. The outer diameter of the guide sleeve 12 corresponds to the lumen of the first guide tube 9.

FIG. 6 is a schematic view of an endoscope 13 comprising a tube part 13.1 and a head part 13.2. This head part has an axial inlet opening for inserting crossed instruments. It also comprises an angled attachment for the connector 13.4 of an image reproduction device (monitor) and flush ports 13.5. The inside of the endoscope, in particular the cylindrical tube part thereof, is designed in a conventional manner, in particular so as to have a working channel having a relatively large diameter in relation to the outer diameter of the tube part and so as to have an optical waveguide or camera and light source and one or two flushing channels arranged on one side of said tube part.

Figure 7A:
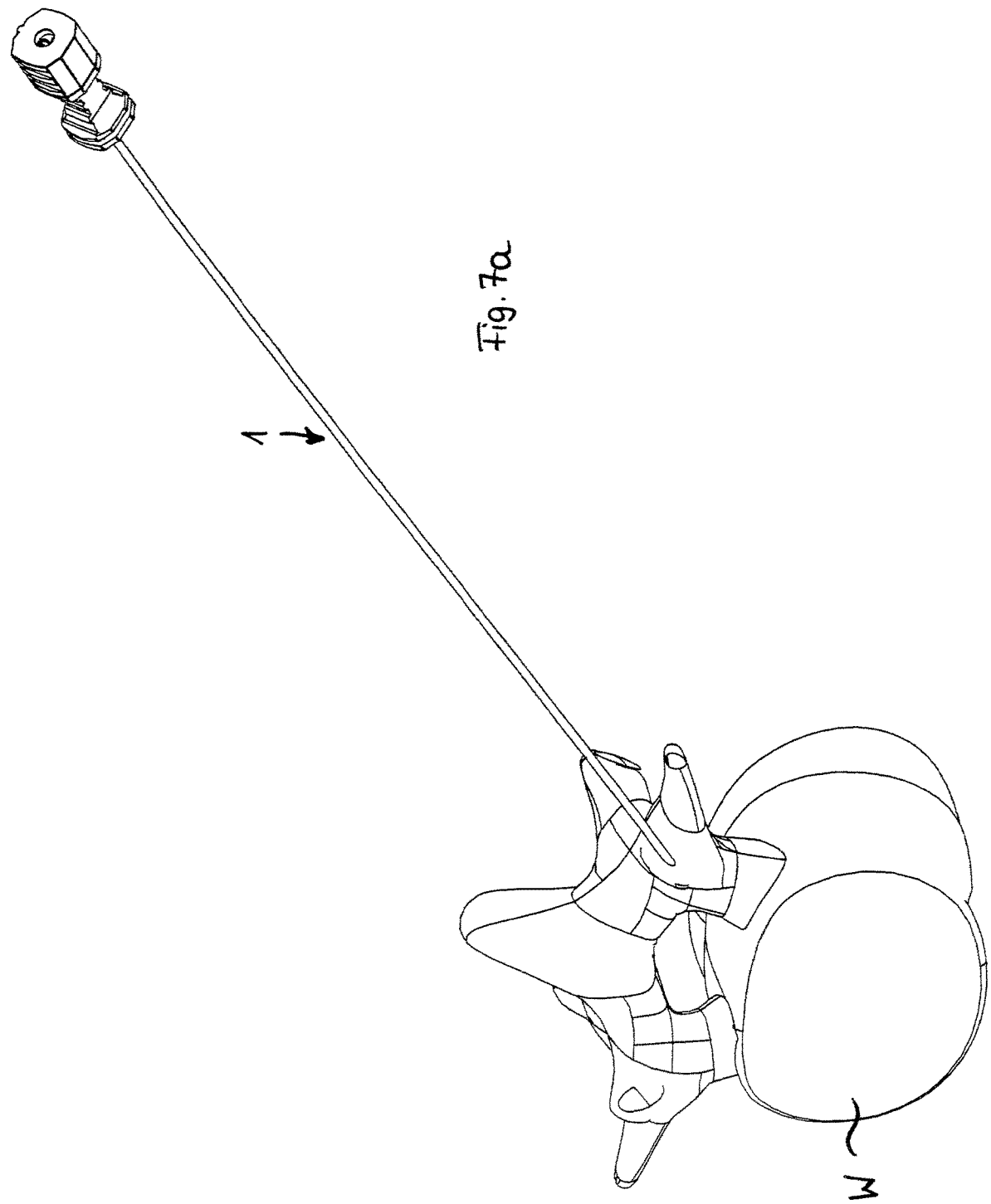
FIG. 7a shows a first method step comprising inserting the distal end of a hollow needle closed by an obturator as far as into the operating site on a vertebra of the method sequence of using the instrument set of FIG. 1.

The method sequence of using the tool set according to the invention, the parts of which include the guide tube 4 of the guide rod 5 and the other parts described with reference to FIG. 1, takes place substantially as follows (FIG. 7):

First, an incision is made in the skin of the patient close to the vertebra W to be worked on. The distally beveled hollow needle 1, together with the stylet located therein, is then inserted through this incision as far as the operating site on the vertebra W under X-ray view (FIG. 7a). The stylet is then removed and the guide wire 3 is also guided through the hollow needle as far as its distal end (FIG. 7b). Hereinafter, the hollow needle 1 is removed and then the guide rod 4 is inserted over the placed guide wire 3 as far as the operating site on the vertebra W (FIG. 7c). A first dilator 6 could then be inserted over the guide tube 4, but this is not the case in the following.

In this respect, reference is made, for example, to WO 2014/146797 A1 or WO 2015/022040 A1. After the guide tube 4 or the dilator 6 has been placed on the outer wall of a bone or vertebra W in a region to be worked on/operated on, as described, the further method sequence is as follows, as shown from FIG. 7d onwards:

The eccentric guide rod 5 is inserted in the distal direction over the guide tube 4 as far as the surface of the bone or vertebra W (FIGS. 7d and 7d1), and then the positioning of the guide tube 4 (and optionally also the dilator 6) relative to the desired operating site, for example the location of osteophytes, is checked under X-ray view and, if the first positioning of the guide tube 4 is not such that, in subsequent steps, a working sleeve to be introduced over said guide tube and/or the guide wire covers or hits a corresponding osteophyte such that it can then be worked on using work instruments to be inserted, the guide tube 4 (optionally together with the dilator) is lifted from the surface of the vertebra W or bone, while the distal tip 5.4 of the eccentric guide rod sits on the vertebra (FIG. 7e and FIG. 7e1).

Hereinafter, the eccentric guide rod 5 is then pivoted about its tip 5.4 sitting on the wall of the vertebra W or bone in the desired manner by means of the lever or grip 5.7, such that its cavity 5.2 and thus the guide tube 4 seated therein reaches the desired operating region, for example the position of an osteophyte at the vertebra W or bone (transition from FIG. 7e to FIG. 7f, FIG. 7/1).

In a further step, the guide tube 4 is then pushed forward again in the distal direction until it rests against the wall of the vertebra/bone W within the guide rod 5, wherein the angular alignment of the guide rod 5 and its grip 5.7 is maintained.

Figure 7H:
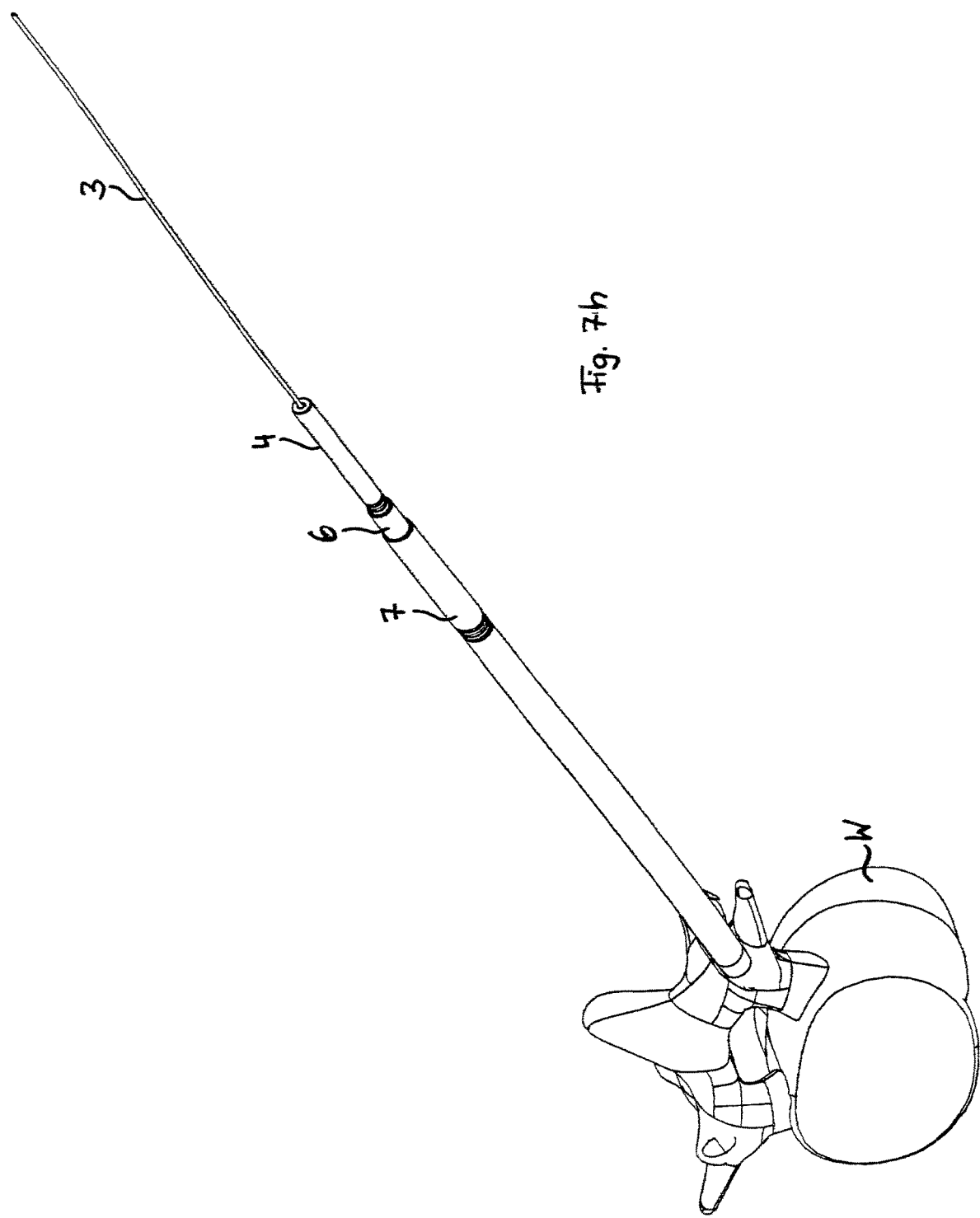
FIG. 7h is a view after the removal of the eccentric guide rod and after the removal of two dilators over the guide tube.
Figure 7J:
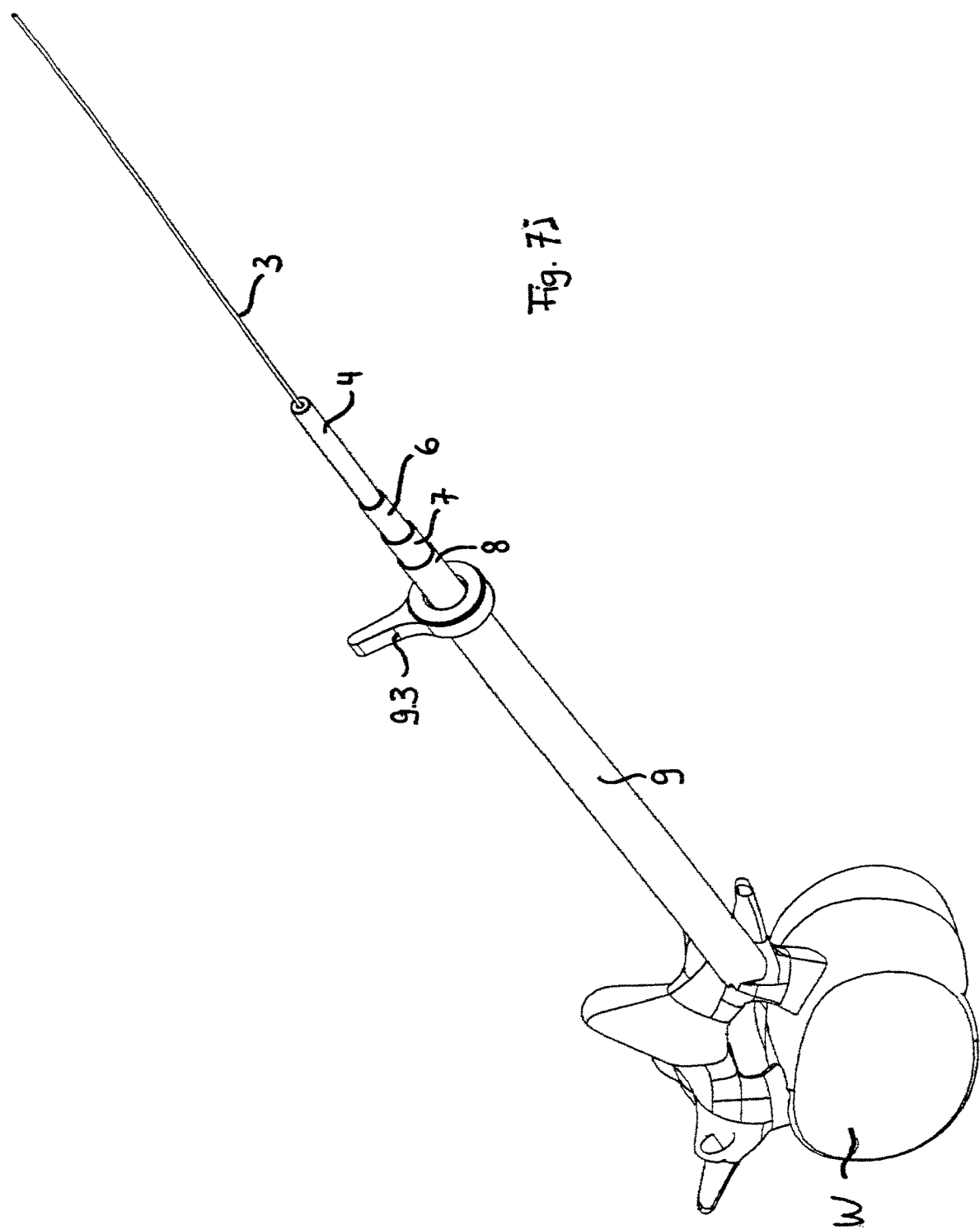
FIG. 7j shows a working sleeve comprising a handgrip, which working sleeve is inserted over the second dilator.

The eccentric guide rod 5 is then retracted in the proximal direction such that its distal end detaches from the wall of the vertebra/bone W (transition from FIG. 7f to FIG. 7g, FIG. 7g1) and is then removed centrally. In order to widen the working channel leading from the body surface to the vertebra/bone, dilators 6, 7, 8 are optionally inserted into the body of the patient as far as the work site on the vertebra W or bone to be treated if a larger cross section of the channel is desired (FIGS. 7h and 7i).

Figure 7M:
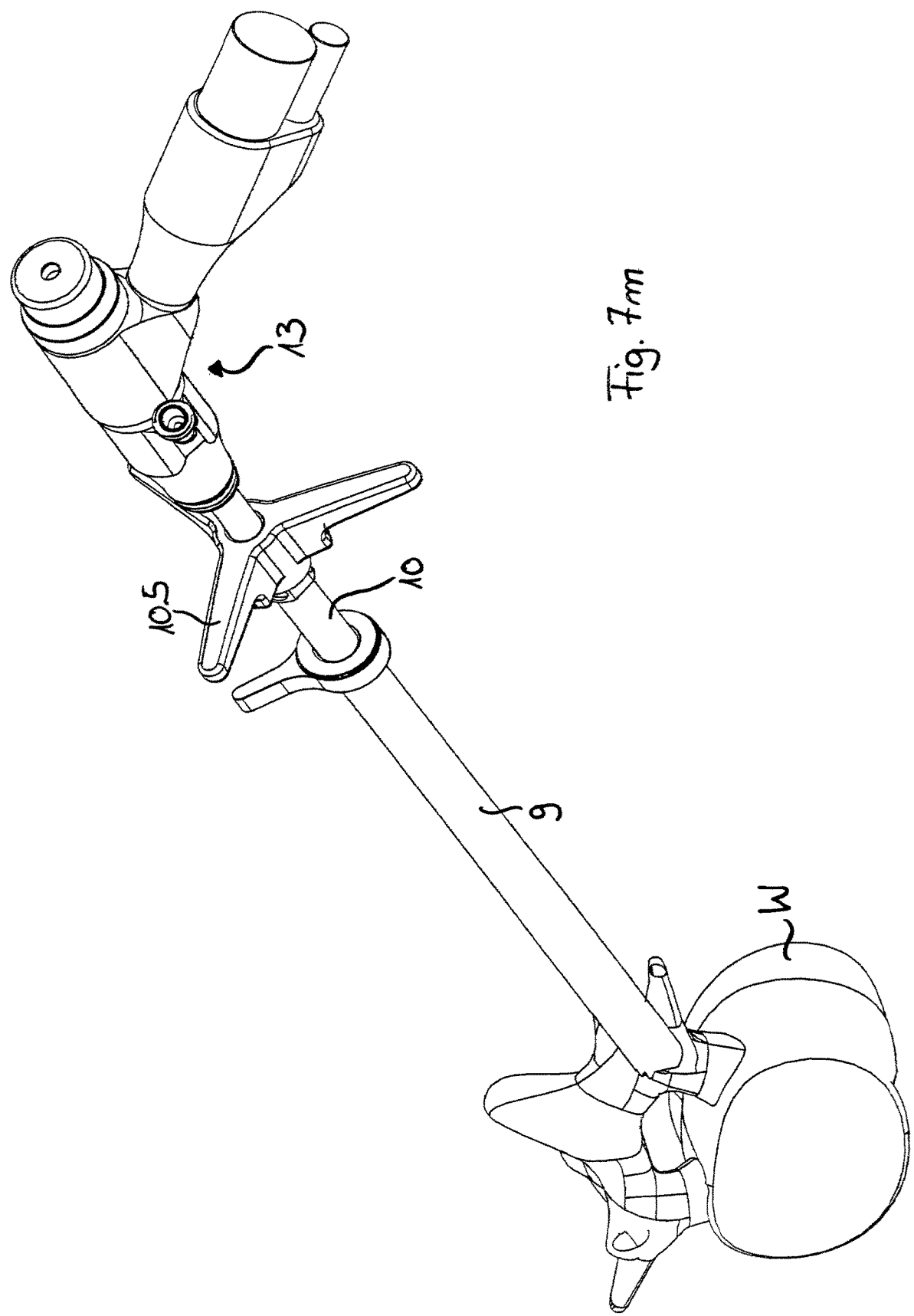
FIG. 7m shows an endoscope inserted through the milling cutter provided with a hollow tube.
Figure 7N:
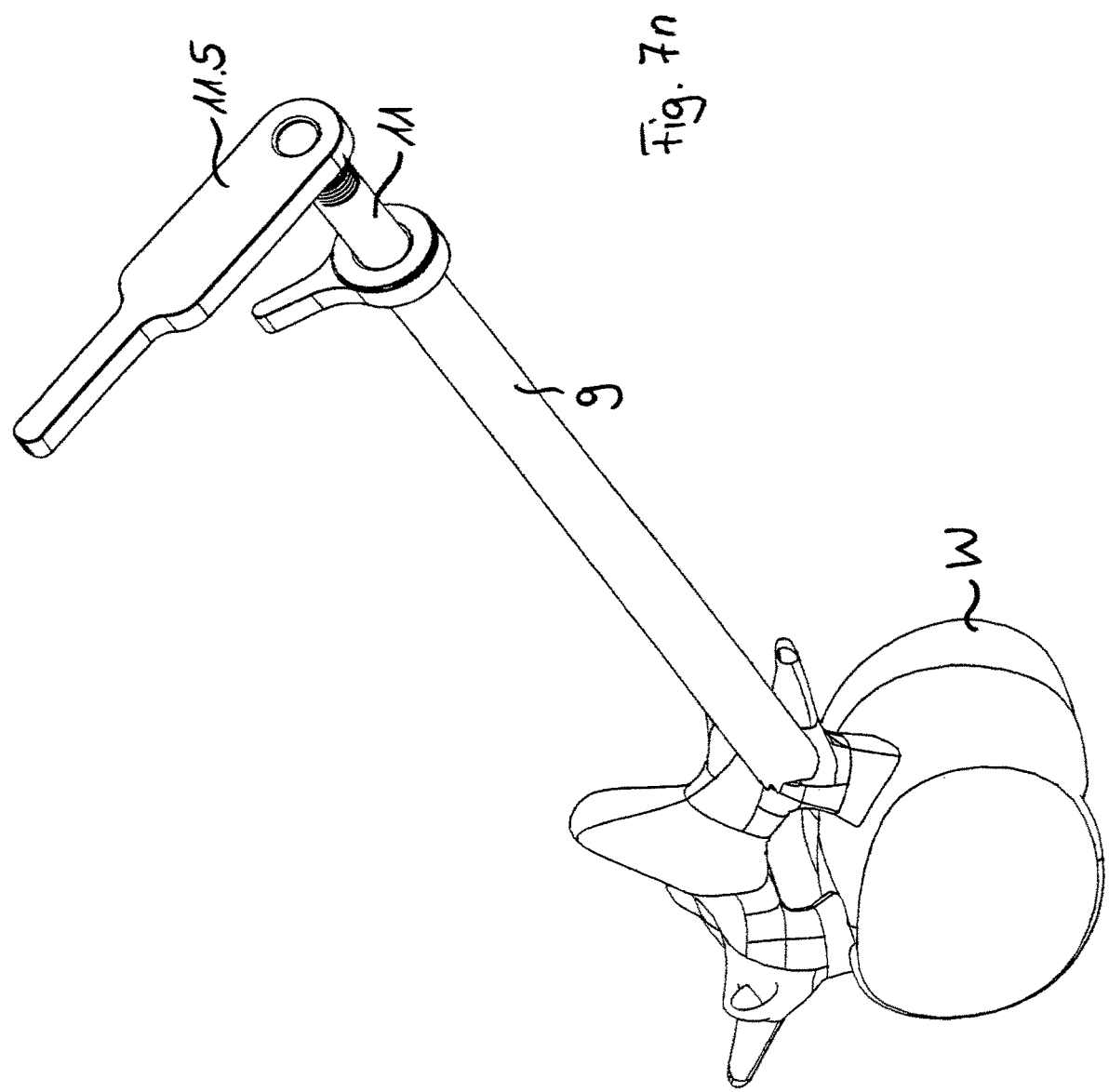
FIG. 7n shows, after the removal of the milling cutter and endoscope, a chisel provided with a handgrip, which chisel is inserted through the working sleeve.
Figure 70:
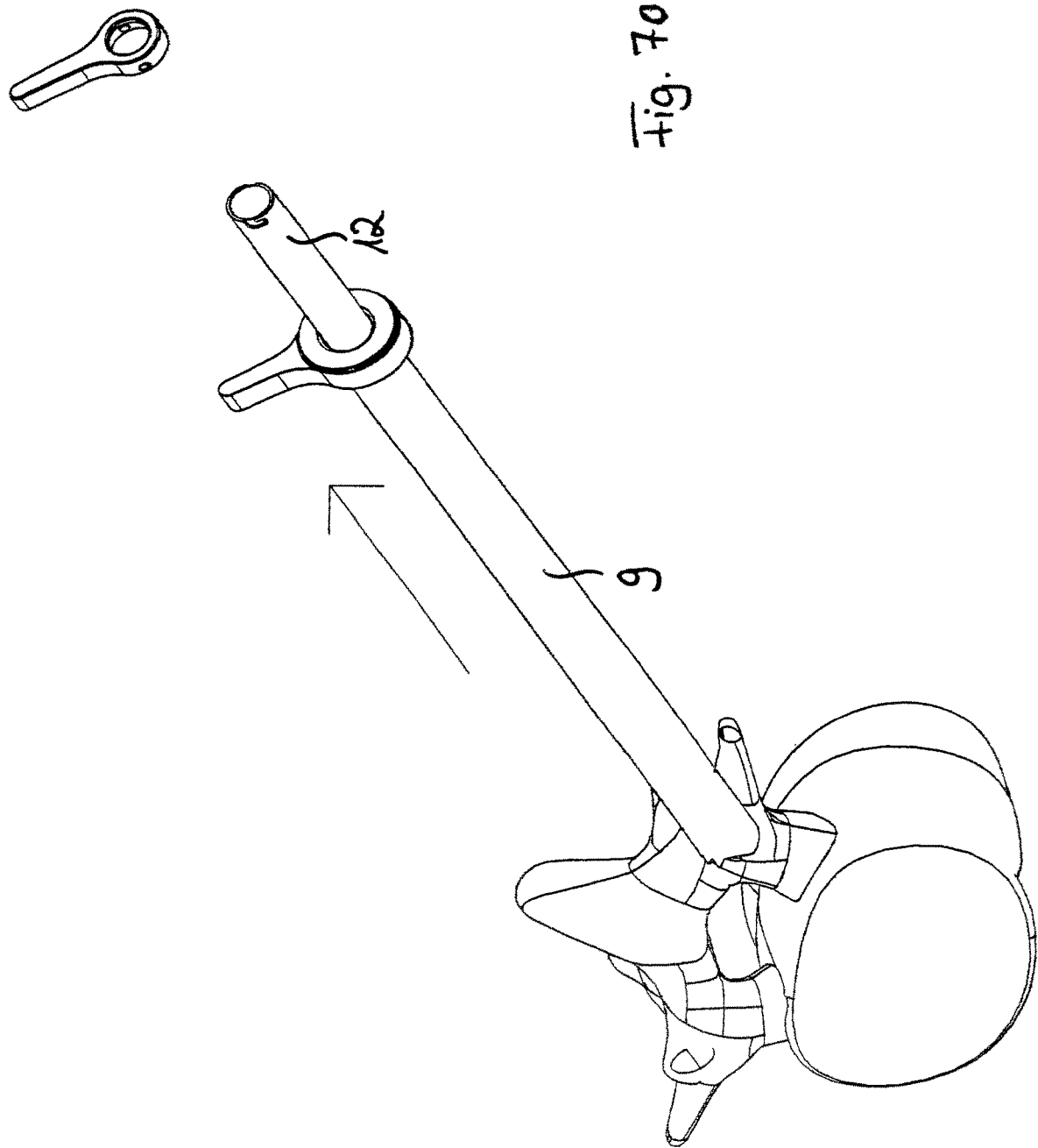

After inserting the working sleeve 9 over the parts 4 and optionally 6, 7, 8 (FIG. 7j), all other tubes such as the guide tube 4 and optionally the dilators 6, 7, 8 are removed (FIG. 7k). Then, if necessary, work tools such as the milling cutter 10 of FIG. 4 or chisel 11 of FIG. 4c or pliers for performing the operation steps on the vertebral body/bone are inserted directly through the working sleeve 9 as far as the operating site (FIGS. 7l to 7n). In order to work with the milling cutter 10 with a cavity in view, an endoscope can be inserted therethrough so as to have its distal end up close to the operating site.

After the removal of the first working sleeve 9 provided distally with teeth (step in FIG. 7o), a differently designed second guide sleeve, as explained with reference to FIG. 5, can optionally be inserted over the chisel 11 and its removable grip 11.5, and, in turn, after the removal of the chisel 11, an endoscope 13 (FIG. 7p) can be inserted through said sleeve through the channel in accordance with further work tools for further work at the operation groove.

As a result of the eccentric guide rod 5 according to the invention, it is therefore possible, if the work instruments have not been inserted accurately in the first method steps, to achieve a lateral offset of the operating site on the vertebra/bone by pivoting the working rod about its tip that is fixed on the surface of the vertebra/bone.

Work instruments 10, 11, optionally also an endoscope 13 comprising a channel for work instruments, can be inserted through the corresponding working sleeve 9 in order to perform the corresponding operation steps, optionally under endoscopic view.

While specific embodiments of the invention have been shown and described in detail to illustrate the application of the principles of the invention, it will be understood that the invention may be embodied otherwise without departing from such principles.

The invention claimed is:

1. Instrument set for spinal operations, comprising:
   at least one dilator;
   a guide cannula;
   a guide rod having a guide rod portion defining an eccentric cavity, the guide rod portion being configured to extend about a first extent of the guide cannula, the first extent extending along a first length in a circumferential direction of the guide cannula, wherein the guide cannula can be received in the cavity of the guide rod, wherein the guide rod portion has a lateral slot opening connected to the cavity, so that the cavity forms a partially cylindrical groove, wherein a width of the lateral slot opening is less than a diameter of the partially cylindrical groove, and the guide rod has one distal tongue which is arranged eccentrically to the cavity of the guide rod, wherein a portion of the at least one distal tongue is adjacent to the guide rod portion, the at least one distal tongue being configured to extend about a second extent of the guide cannula, the second extent extending along a second length in the circumferential direction of the guide cannula, the second length being less than the first length.

2. Set according to claim 1, wherein the cavity is eccentric with respect to the outer contour and/or the central axis of the outer contour of the guide rod.

3. Set according to claim 1, wherein the distal tongue of the guide rod is arranged eccentrically with respect to a central axis of the guide rod.

4. Set according to claim 1, wherein the at least one distal tongue has a distal tongue opening in communication with the cavity, the at least one distal tongue comprising edges defining a convex arcuate shape of the at least one distal tongue opening.

5. Set according to claim 4, wherein the at least one distal tongue comprises a distal tip located at a spaced location from the portion of the at least one distal tongue, wherein a height of the distal tongue decreases from the portion of the at least one distal tongue to the distal tip.

6. Set according to claim 1, wherein the inner wall surface of the guide rod that surrounds the cavity and the groove is in the shape of a cylinder jacket or a partial cylinder jacket.

7. Set according to claim 1, wherein the outer wall surface of the guide rod is in the shape of a cylinder jacket or partial cylinder jacket.

8. Set according to claim 1, wherein the slot opening of the cavity or the groove of the guide rod is diagonally opposite the tongue.

9. Set according to claim 1, wherein the distal tongue of the guide rod has opposing partially arcuate edges, the distal ends of which lead into a tip of the tongue.

10. Set according to claim 1, further comprising a working sleeve comprising a longitudinally extending, in particular cylindrical cavity which has a cross section that is at least the same as the cross section of the guide tube, preferably as the cross section of the guide rod.

11. Set according to claim 10, wherein the working sleeve has a row of teeth on its distal end face.

12. Set according to claim 11, wherein the row of teeth extends over at least half of the circumference of the working sleeve.

13. Set according to claim 11, wherein the teeth of the row of teeth are asymmetrical, the row of teeth extending about an extent of the working sleeve, the extent of the working sleeve defining a half of the circumference of the working sleeve.

14. Set according to claim 11, wherein a first flank of the teeth is designed as a flat S inclined toward the distal tip of a tooth.

15. Set according to claim 11, wherein a second flank is oriented axially parallel.

16. Set according to claim 10, wherein a distal lip extends over part of the circumference of the working sleeve.

17. Set according to claim 16, wherein the tips of the teeth and the end face of the lip are at the same axial height.

18. Set according to claim 1, further comprising a hollow needle comprising a stylet and/or a guide wire, transverse dimensions of the stylet and/or guide wire preferably being adapted to the lumen of the cavity of the hollow needle.

19. Set according to claim 1, wherein the at least one dilator comprises dilators comprising lumina adapted to the guide tube and/or guide rod or to one another.

20. Set according to claim 1, further comprising work tools such as milling cutters and the chisel, the radial dimensions of which are adapted in particular to the lumen of the working tube.

21. Method for performing operations, in particular on the outside of vertebral bodies or bones, wherein, after a guide tube has been inserted from the body surface of a patient as far as the surface of a vertebral body or bone, a guide rod comprising an eccentrically formed cavity is inserted over the guide tube into the body of the patient as far as the surface of the vertebral body or bone, in that the position of the distal end of the guide cannula relative to an intended position is checked, generally under X-ray view, if the intended operating region does not match the position of the distal end of the guide tube on the vertebral body or bone, a distal tip formed eccentrically at the distal end of the guide rod is pressed against the surface of the vertebral body or bone, the guide tube within the guide rod is retracted in a proximal direction, the guide rod together with the guide tube located therein is pivoted about its distal tip in order to pivot a cavity of the guide rod over the intended operating region or to move closer to the operating region, and the guide tube within the guide rod is subsequently moved again distally toward the surface of the vertebral body or bone, the guide rod comprising a distal tongue and a guide rod portion, the guide portion defining the cavity, the guide portion being configured to extend about a first extent of the guide tube comprising a first length extending in a circumferential direction of the guide tube, wherein a portion of the at least one distal tongue is adjacent to the guide rod portion, the at least one distal tongue being configured to extend about a second extent of the guide tube comprising a second length extending in the circumferential direction of the guide tube, the second circumferential length being less than the first circumferential length.

22. Method according to claim 21, wherein a guide rod comprising a cavity arranged eccentrically in its outer contour and/or the axis of symmetry of its outer contour is inserted into the body of the patient.

23. Method according to claim 21, wherein, without or after removing the guide rod over the guide tube or if the guide rod is not removed, a working sleeve is inserted, over said guide rod, into the body of the patient in a distal direction as far as the surface of the vertebral body or bone and anchored on the surface the vertebral body or bone, and the guide tube and optionally the guide rod are removed from the working sleeve.

24. Method according to claim 21, wherein one or more dilators are firstly introduced over the guide tube or guide rod as far as the vertebral body and the working sleeve is subsequently inserted over the inserted dilator having the largest diameter.

25. Method according to claim 21, wherein firstly, optionally after making a skin incision, a hollow needle having an inserted stylet is inserted into the body of the patient as far as the vertebral body, then the stylet is removed and a guide wire is inserted through the hollow needle, and then, after removing the hollow needle, the guide tube is inserted over the guide wire as far as the vertebral body and finally the further steps of the method are carried out.

26. Method according to claim 21, wherein at least one work instrument is inserted through the working sleeve as far as the operating site on the vertebral body or bone, and the operation to be performed is carried out on the vertebral or bone surface.

27. Method according to claim 26, wherein the shaft of an endoscope is inserted through an elongate cavity of the work instrument.

28. Method according to claim 21, wherein an endoscope is firstly inserted through the working sleeve and then a work instrument is inserted through an elongate cavity of the endoscope as far as the surface of the vertebral body or bone, and a surgical step is carried out under endoscopic view.

* * * * *